United States Patent
Kurokawa et al.

(10) Patent No.: US 6,656,337 B2
(45) Date of Patent: Dec. 2, 2003

(54) GAS CONCENTRATION MEASURING APPARATUS COMPENSATING FOR ERROR COMPONENT OF OUTPUT SIGNAL

(75) Inventors: Eiichi Kurokawa, Okazaki (JP); Satoshi Hada, Kariya (JP); Toshiyuki Suzuki, Handa (JP); Mitsunobu Niwa, Kariya (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/984,663

(22) Filed: Oct. 30, 2001

(65) Prior Publication Data

US 2002/0050455 A1 May 2, 2002

(30) Foreign Application Priority Data

Oct. 31, 2000 (JP) .......................... 2000-333319
Jul. 5, 2001 (JP) .......................... 2001-204728

(51) Int. Cl.[7] .................... G01N 27/407; G01N 27/41
(52) U.S. Cl. .................... 204/425; 204/401; 204/426; 204/427; 205/781; 73/23.31
(58) Field of Search .................. 204/424, 425, 204/426, 427, 401; 205/781; 73/23.31

(56) References Cited

U.S. PATENT DOCUMENTS 5,034,112 A * 7/1991 Murase et al. .............. 204/406
5,993,641 A * 11/1999 Okazaki et al. ........... 205/784.5
6,295,862 B1 * 10/2001 Kurokawa et al. ......... 73/31.05

FOREIGN PATENT DOCUMENTS

EP 0678740 A1 * 10/1995
EP 0841562 A2 * 5/1998

OTHER PUBLICATIONS

Sugaya et al; "Measurement of Nox and $O_2$ Concentration in Exhaust Gas Using Newly Developed Nox Sensor"; May 1997; pp. 277–280; Academic Lecture Preliminary Report, Automotive Technical Meeting Corporation.
Kato et al; "Performance of Thick Film Nox Sensor on Diesel and Gasoline Engines"; 1997; pp. 199–206; Electronic Engine Controls.

* cited by examiner

Primary Examiner—Kaj K. Olsen
(74) Attorney, Agent, or Firm—Nixon & Vanderhye, PC

(57) ABSTRACT

A gas concentration measuring apparatus is provided which includes a gas concentration sensor consisting of a pump cell, a sensor cell, and a monitor cell. The pump cell works to determine the concentration of $O_2$. The sensor cell works to decompose an oxygen containing gas such as NOx and provide an output indicative of the concentration of NOx. The apparatus also includes an applying voltage determining circuit which looks up a predetermined voltage-to-current relation to determine a target voltage to be applied to the pump cell as a function of the current produced by the pump cell so as to preclude the pump cell from decomposing the oxygen containing gas component, thereby minimizing an error in determining the concentration of oxygen containing gas as a function of the output of the sensor cell.

32 Claims, 20 Drawing Sheets

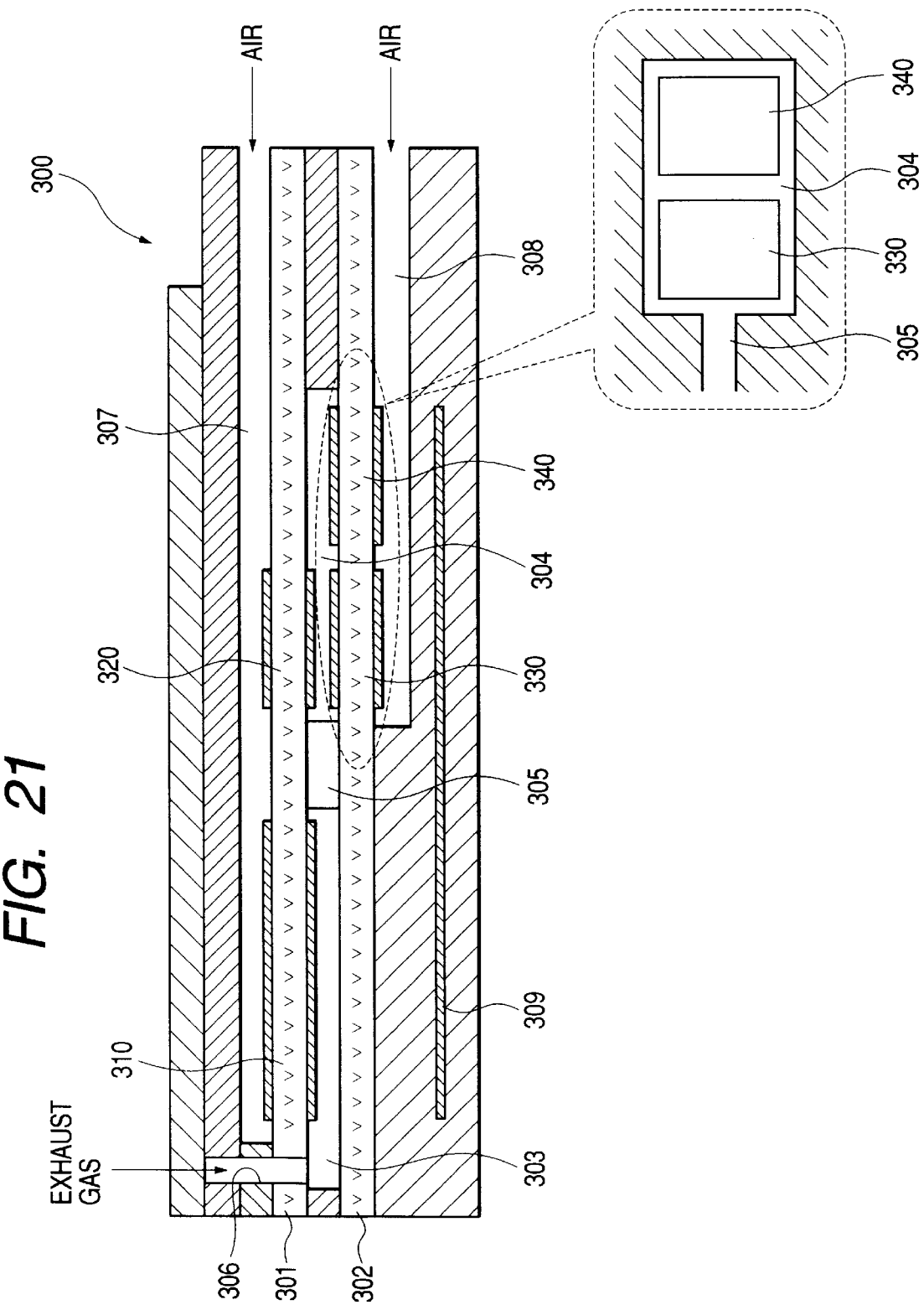

GAS CONCENTRATION MEASURING APPARATUS COMPENSATING FOR ERROR COMPONENT OF OUTPUT SIGNAL

BACKGROUND OF THE INVENTION

1. Technical Field of the Invention

The present invention relates generally to a gas concentration sensor for measuring the concentration of gases which may be employed in an air-fuel ratio control system for automotive vehicles, and more particularly to a limiting current type gas concentration measuring apparatus equipped with a limiting current type gas sensor which is designed to compensate for an error in determining the concentration of a gas.

2. Background Art

Limiting current type gas concentration sensors are known which are used for measuring NOx contained in exhaust gasses of automotive engine. There is used one of such gas concentration sensors which includes a pump cell and a sensor cell. The pump cell works to pump oxygen ($O_2$) contained in gasses admitted into a gas chamber out of the sensor or to pump oxygen ($O_2$) of outside gasses into the gas chamber. The sensor cell works to measure the concentration of NOx contained in the gasses after passing through the pump cell. The pump cell and the sensor cell are designed to produce current signals indicative of the concentration of oxygen and NOx upon application of voltage thereto.

Another type of gas concentration sensor is known which includes a monitor cell in addition to the pump cell and the sensor cell. The monitor cell works to produce an electromotive force as a function of the concentration of oxygen within the gas chamber. A control system is also proposed which controls the voltage to be applied to the pump cell of such a three-cell gas concentration sensor under PID feedback (e.g., Academic Lecture Preliminary Report, Automotive Technical Meeting Corporation and SAE 970858). Specifically, this system is designed to determine the voltage to be applied to the pump cell based on a difference between an actual electromotive force produced by the monitor cell and a target one predetermined for keeping the concentration of oxygen at a lower level within the gas chamber.

The measurement of the concentration of exhaust gasses in the three-cell gas concentration sensor is achieved by introducing the exhaust gasses from the pump cell toward the monitor cell. Thus, when the concentration of exhaust gasses varies, a difference in concentration of the exhaust gasses between the pump cell and the monitor cell is resulted from a lag caused by the time required for the exhaust gasses to flow from the pump cell to the monitor cell. The time will, therefore, be consumed until the concentration of the exhaust gasses at the monitor cell agrees with that at the pump cell. This problem will be objectionable in a gas concentration sensor in which an orifice is provided between the pump cell and the monitor cell. Accordingly, when the voltage to be applied to the pump cell is feedback controlled as a function of the electromotive force produced by the monitor cell, a shift in feedback control phase may result in oscillation.

For instance, when it is required to change the exhaust gasses to a lean side, so that a large quantity of oxygen flows into the gas chamber, it is difficult for the monitor cell to detect such changing, thereby resulting in insufficient quantity of oxygen pumped by the pump cell under the feedback control using an output of the monitor cell. A large quantity of oxygen, thus, remains undesirably within the gas chamber. Subsequently, when the lean condition of the exhaust gasses is detected based on the output of the monitor cell, it will cause an excess voltage to be applied to the pump cell to pump the residual oxygen out of the gas chamber thereinto, after which the monitor cell continues to provide an output indicative of the lean condition for a while. After it is found that too much oxygen has been pumped out of the gas chamber, the voltage applied to the pump cell is change rapidly to a lower level.

The above phenomenon is repeated, thereby leading to oscillation of a control system applying the voltage to the pump cell, so that a residual quantity of oxygen within the gas chamber changes greatly in a cycle. This may cause the quantity of oxygen contained in the exhaust gasses flowing to the sensor cell to increase or the pump cell to decompose NOx undesirably. When the former is taken place, the sensor cell decomposes the increased quantity of oxygen to increase an offset current contained in an output thereof. When the latter is taken place, it results in insufficient quantity of NOx contained in the exhaust gasses flowing to the sensor cell, thus producing an error in determining the concentration of NOx.

Additionally, when the response rate of each cell is changed with a change in temperature of the exhaust gasses or deterioration of the cell, a residual quantity of oxygen within the gas chamber also changes, thus resulting in a decrease in accuracy of determining the concentration of NOx. For instance, in a case where enriched exhaust gases are admitted into the gas chamber, and a rich gas component (e.g., HC) sticks to an electrode of the monitor cell, the monitor cell continues to produce an output indicative of the rich condition in error even after the exhaust gasses is changed to the lean side. This causes the voltage applied to the pump cell to be controlled so that oxygen ($O_2$) of outside gasses may be pumped into the gas chamber. Afterwards, when the rich gas component sticking to the electrode of the monitor cell reacts with the oxygen and peels, the monitor cell produces an output indicative of changing to the lean side, so that the voltage to be applied to the pump cell is so controlled as to pump the oxygen out of the gas chamber. At this time, the concentration of oxygen within the gas chamber is increased extremely, thus resulting in application of an excess voltage to the pump cell. Similarly, in a case where the exhaust gases are switched from lean to rich, and a lean gas component (e.g., $O_2$) sticks to the electrode of the monitor cell, the monitor cell continues to produce an output indicative of the lean condition in error even after the exhaust gasses is changed to the rich side. This causes the voltage applied to the pump cell to be controlled so that oxygen ($O_2$) may be pumped out of the gas chamber. Specifically, an excess voltage is applied to the pump cell so as to decompose NOx as well as $O_2$.

The above event is repeated, thereby leading to oscillation of the control system applying the voltage to the pump cell, so that a residual quantity of oxygen ($O_2$) within the gas chamber changes greatly in a cycle. This results in decreased accuracy of determining the concentration of NOx.

SUMMARY OF THE INVENTION

It is therefore a principal object of the present invention to avoid the disadvantages of the prior art.

It is another object of the present invention to provide a gas concentration measuring apparatus designed to eliminate an error in determining the concentration of a specified gas component of measurement gases.

According to one aspect of the invention, there is provided a gas concentration measuring apparatus which may be employed with an automotive control system designed to control the quantity of fuel injected into an internal combustion gasoline engine as a function of an output of the gas concentration measuring apparatus under feedback (F/B) control to bring the air-fuel (A/F) ratio into agreement with a target value. The gas concentration measuring apparatus comprises: (a) a gas concentration sensor including a gas chamber, a first cell responsive to application of a voltage to pump thereinto oxygen molecules contained in gasses admitted into the gas chamber and discharge the pumped oxygen molecules to produce an electric current indicative of a concentration of the oxygen molecules, a second cell working to determine a concentration of a specified oxygen containing gas component contained in the gasses having passed through the first cell, and a monitor cell working to monitor a concentration of residual oxygen molecules within the gas chamber and provide an output indicative thereof; (b) an applying voltage determining circuit looking up a predetermined voltage-to-current relation to determine a target voltage to be applied to the first cell as a function of the electric current produced by the first cell so as to preclude the first cell from decomposing the specified oxygen containing gas component; and (c) an applying voltage controlling circuit working to apply the target voltage determined by the applying voltage determining circuit to the first cell.

Unlike a conventional system in which an electromotive force produced by a monitor cell is brought into agreement with a target one under feedback control using PID techniques, the use of the voltage-to-current relation to determine the target voltage to be applied to the first cell in the gas concentration measuring apparatus of the invention eliminates the problem that the applying voltage controlling circuit oscillates due to a response delay of the monitor cell, thereby resulting in a great cyclic change in residual quantity of oxygen within the gas chamber.

In a conventional system in which the voltage to be applied to the first cell is determined using an output of the monitor cell under feedback control, the voltage applied to the first cell and outputs of the first cell, the second cell, and the monitor cell when the concentration of gasses changes to a lean side so that the concentration of oxygen increases are varied as shown in FIG. 22(b). Specifically, an undesirable time is consumed in detecting a change in concentration of gasses using the output of the monitor cell. The avoidance of oscillation arising from a difference in response speed between the first cell and the monitor cell requires decreasing a feedback gain, so that the voltage applied to the first cell changes slowly, which results in a lack of discharge of oxygen from the gas chamber. An excess current, thus, flows through the second cell. It is, in practice, difficult to determine the concentration of gasses until the outputs of the second cell and the monitor cell are in steady state.

In the gas concentration measuring apparatus of the invention, when the current produced by the first cell changes with a change in concentration of the gasses, the voltage applied to the first cell is, as can be seen from FIG. 22(a), adjusted to a target one immediately, thus preventing the concentration of oxygen from being increased undesirably within the gas chamber, so that the output of the monitor cell remains unchanged. The second cell, thus, produces the current indicative of the concentration of the specified oxygen containing gas quickly.

In the preferred mode of the invention, the gas chamber includes a first chamber to which the first cell is exposed, a second chamber to which the monitor cell is exposed, and a diffusion path communicating between the first and second chambers.

The predetermined voltage-to-current relation is listed in a map. The applying voltage determining circuit determines the target voltage to be applied to the first cell by look-up using the map.

An applying voltage correcting circuit may further be provided which works to correct the target voltage to be applied to the first cell as a function of a given residual oxygen variation factor of a variation in residual quantity of oxygen within the gas chamber after the first cell pumps the oxygen molecules. The residual oxygen variation factor is, for example, a change in concentration of the gasses, a change in activity of the first cell, or an inherent error of the sensor.

The applying voltage correcting circuit may correct the target voltage based on the output of the monitor cell.

The first cell is formed in a solid electrolyte element. A resistance measuring circuit may also be provided which works to measure a resistance of the solid electrolyte element. The applying voltage correcting circuit may correct the target voltage as a function of the resistance measured by the resistance measuring circuit.

The second cell outputs a current as a function of the concentration of the specified oxygen containing gas component. A second cell output correcting circuit may be provided which works to correct the current outputted from the second cell based on the output of the monitor cell.

A change rate determining circuit may be provided which works to determine a variable rate at which the target voltage applied to the first cell is to be changed. When the concentration of the gasses changes, so that the concentration of the oxygen molecules changes. The electric current produced by the first cell is, thus changed, thereby causing the target voltage to be applied to the first cell to be changed. In this case, the modification of the rate of application of the target voltage enables the oxygen molecules to be pump into or out of the gas chamber at an increased velocity.

The change rate determining circuit may increase the variable rate as a difference between an actual voltage applied to the first cell and the target voltage to be applied to the first cell increases.

The change rate determining circuit may determine the variable rate by setting a cycle in which the target voltage is changed. The change rate determining circuit may increase the cycle as a difference between an actual voltage applied to the first cell and the target voltage to be applied to the first cell is decreased. This results in an advance in convergence of the voltage applied to the first cell on the target one. The adjustment of the variable rate may eliminate the effect of a peak current produced when the voltage applied to the first cell is changed. Specifically, when the voltage applied to the first cell is changed, a peak current (i.e., tailing) is produced as an output of the first cell, but the adjustment of the variable rate enables the target voltage to be applied to the first cell to be changed after the peak current disappears. FIG. 23 shows an equivalent circuit of the gas concentration sensor. Rg indicates the resistance of particles of a solid electrolyte (zirconia) to oxygen irons. Rh and Ch indicate a grain boundary resistance and a grain boundary capacitance on a boundary face of the solid electrolyte, respectively. Rf and Cf indicate an electrode boundary face resistance and an electrode boundary face capacitance. When the voltage to be applied to the gas concentration sensor is, as shown in FIG. 24, changed, it will cause a peak current to be produced immediately due to charges stored by the capacitances Ch and Cf. The above adjustment of the change rate enables the voltage applied to the first cell to be controlled without the influence of the capacitances of the gas concentration sensor.

A current measuring range is defined in which the electric current produced by the first cell is to be measured. The voltage-to-current relation is defined by a target applying voltage line representing the target applying voltage to be applied to the first cell in terms of the electric current produced by the first cell. The target applying voltage line includes a segment which changes with a change in electric current produced by the first cell at a first inclination substantially depending upon a resistance of the first cell within the current measuring range. Within an outside range defined outside the current measuring range, the target applying voltage line includes a segment which changes at a second inclination reverse in sign to the first inclination. This avoids undesirable generation of heat arising from an excess increase in output of the first cell.

A higher voltage may be applied to the first cell for a period of time following energization of the gas concentration sensor. When the gas concentration sensor is started, the gas chamber is filled with the air, so that an excess quantity of oxygen exist in the gas chamber. The application of the higher voltage causes the excess quantity of oxygen to be discharged out of the gas chamber quickly.

When the output of the monitor cell falls out of a specified range immediately after the gas concentration is energized, the applying voltage controlling circuit applies the higher voltage to the first cell.

According to the second aspect of the invention, there is provided a gas concentration measuring apparatus which comprises: (a) a gas concentration sensor including a gas chamber, a first cell responsive to application of a voltage to pump thereinto oxygen molecules contained in gasses admitted into the gas chamber and discharge the pumped oxygen molecules to produce an electric current indicative of a concentration of the oxygen molecules, a second cell working to determine a concentration of a specified oxygen containing gas component contained in the gasses having passed through the first cell, and a monitor cell working to monitor a concentration of residual oxygen molecules within the gas chamber and provide an output indicative thereof; (b) an applying voltage correcting circuit working to determine a target voltage to be applied to the first cell by looking up a predetermined voltage-to-current relation as a function of the electric current produced by the first cell, the applying voltage correcting circuit correcting one of the target voltage and the predetermined voltage-to-current relation as a function of the output of the monitor cell; and (c) an applying voltage controlling circuit working to control voltage applied to the first cell into agreement with the target voltage determined by the applying voltage correcting circuit. This enables a residual quantity of the oxygen within the gas chamber to be kept constant regardless of a change in activity of the first cell, thus resulting in improved accuracy of determining the concentration of the specified oxygen containing gas.

In the preferred mode of the invention, the voltage-to-current relation is defined in a map by a target applying voltage line which represents the target applying voltage to be applied to the first cell in terms of the electric current produced by the first cell. The applying voltage correcting circuit corrects the voltage-to-current relation by changing an inclination of the target applying voltage line defined in the map as a function of the output of the monitor cell. For instance, as the output of the monitor cell increases, the inclination is preferably decreased, thereby increasing the target voltage to be applied to the first cell, so that a residual quantity of oxygen within the gas chamber is decreased.

The applying voltage correcting circuit may alternatively correct the voltage-to-current relation by changing an offset of the target applying voltage line in terms of the electric current produced by the first cell as a function of the output of the monitor cell. For instance, as the output of the monitor cell increases, the offset is preferably increased, thereby increasing the target voltage to be applied to the first cell, so that a residual quantity of oxygen within the gas chamber is decreased.

The applying voltage correcting circuit may correct the target voltage to be applied to the first cell so as to bring the output of the monitor cell into agreement with a target value required for keeping the concentration of oxygen molecules at a given level within the gas chamber.

The correction of the target voltage to be applied to the first cell is performed in a cycle longer than that in which the voltage applied to the first cell is controlled by the applying voltage controlling circuit in view of a change in response arising from deterioration or an inherent error of the sensor.

According to the third aspect of the invention, there is provided a gas concentration measuring apparatus which comprises: (a) a gas concentration sensor including a gas chamber, a first cell responsive to application of a voltage to pump thereinto oxygen molecules contained in gasses admitted into the gas chamber and discharge the pumped oxygen molecules to produce an electric current indicative of a concentration of the oxygen molecules, a second cell working to produce an electric current for determining a concentration of a specified oxygen containing gas component contained in the gasses having passed through the first cell, and a monitor cell working to monitor a concentration of residual oxygen molecules within the gas chamber and provide an output indicative thereof; (b) an applying voltage determining circuit looking up a predetermined voltage-to-current relation to determine a target voltage to be applied to the first cell as a function of the electric current produced by the first cell so as to preclude the first cell from decomposing the specified oxygen containing gas component; and (c) a second cell output correcting circuit working to correct the electric current outputted by the second cell as a function of the output of the monitor cell. This avoid an error in determining the concentration of the specified oxygen containing gas arising from a change in residual quantity of oxygen within the gas chamber.

In the preferred mode of the invention, the second cell output correcting circuit subtracts a current value equivalent to the output of the monitor cell representing the concentration of residual oxygen molecules from the electric current produced by the second cell.

The second cell output correcting circuit corrects the electric current produced by the second cell and the output of the monitor cell as a function of a difference in catalysis between the second cell and the monitor cell, after which the second cell output correcting circuit subtracts the current value equivalent to the output of the monitor cell representing the concentration of residual oxygen molecules from the electric current produced by the second cell.

The second cell and the monitor cell are disposed adjacent to each other and exposed to a second chamber formed downstream of the first cell.

According to the fourth aspect of the invention, there is provided a gas concentration measuring apparatus comprising: (a) a gas concentration sensor including a gas chamber, a first cell responsive to application of a voltage to pump thereinto oxygen molecules contained in gasses admitted into the gas chamber and discharge the pumped oxygen molecules to produce an electric current indicative of a concentration of the oxygen molecules, a second cell working to output an electric current for determining a concentration of a specified oxygen containing gas component contained in the gasses having passed through the first cell, and a monitor cell working to monitor a concentration of residual oxygen molecules within the gas chamber and provide an output indicative thereof; (b) an applying voltage determining circuit working to determine a target voltage to be applied to the first cell by looking up a predetermined voltage-to-current relation as a function of the electric current produced by the first cell; (c) a first correcting circuit working to correct one of the target voltage and the predetermined voltage-to-current relation as a function of the output of the monitor cell so as to preclude the first cell from decomposing the specified oxygen containing gas component; (d) an applying voltage controlling circuit working to control voltage applied to the first cell into agreement with the target voltage provided by the applying voltage correcting circuit; and (e) a second correcting circuit working to correct the electric current produced by the second cell as a function of the output of the monitor cell to determine the concentration of the specified oxygen containing gas component. This avoid an error in determining the concentration of the specified oxygen containing gas arising from a change in residual quantity of oxygen within the gas chamber.

In the preferred mode of the invention, the correction of the target voltage to be applied to the first cell is performed by the first correcting circuit in a cycle longer than that in which the voltage applied to the first cell is controlled by the applying voltage controlling circuit.

When the output of the monitor cell is brought into agreement with a target value or falls within a range around the target value under control of the target voltage applied to the first cell by the applying voltage controlling circuit, the second correcting circuit corrects the electric current produced by the second cell based on the output of the monitor cell.

According to the fifth aspect of the invention, there is provided a gas concentration measuring apparatus which comprises: (a) a gas concentration sensor including a gas chamber, a first cell responsive to application of a voltage to pump thereinto oxygen molecules contained in gasses admitted into the gas chamber and discharge the pumped oxygen molecules to produce an electric current indicative of a concentration of the oxygen molecules, a second cell working to determine a concentration of a specified oxygen containing gas component contained in the gasses having passed through the first cell, and a monitor cell working to monitor a concentration of residual oxygen molecules within the gas chamber and provide an output indicative thereof, the first cell being formed in a solid electrolyte element; (b) a resistance determining circuit working to determine a resistance of the solid electrolyte element; (c) an applying voltage determining circuit working to determine a target voltage to be applied to the first cell by looking up a predetermined voltage-to-current relation as a function of the electric current produced by the first cell; (d) an applying voltage correcting circuit correcting one of the target voltage and the predetermined voltage-to-current relation as a function of the resistance determined by the resistance determining circuit; and (e) an applying voltage controlling circuit working to control voltage applied to the first cell into agreement with the target voltage provided by the applying voltage correcting circuit. This avoid an error in determining the concentration of the specified oxygen containing gas arising from a change in residual quantity of oxygen within the gas chamber.

In the preferred mode of the invention, the voltage-to-current relation is defined in a map by a target applying voltage line which represents the target applying voltage to be applied to the first cell in terms of the electric current produced by the first cell. The applying voltage correcting circuit corrects the voltage-to-current relation by changing an inclination of the target applying voltage line defined in the map as a function of the resistance of the first cell.

The voltage-to-current relation is defined in a map by a target applying voltage line which represents the target applying voltage to be applied to the first cell in terms of the electric current produced by the first cell. The applying voltage correcting circuit corrects the voltage-to-current relation by changing an offset of the target applying voltage line in terms of the electric current produced by the first cell as a function of the resistance of the first cell.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 3(*b*) shows an example of a map listing an applied voltage-to-output current relation of a monitor cell;

FIG. 3(*c*) shows an example of a map listing an applied voltage-to-output current relation of a sensor cell;

FIG. 5(*b*) shows a variation in applied voltage-to-output current relation of a monitor cell with a variation in impedance of a pump cell;

FIG. 5(*c*) shows a variation in applied voltage-to-output current relation of a sensor cell with a variation in impedance of a pump cell;

FIG. 21 is a sectional view which shows a modification of a gas concentration measuring sensor;

DESCRIPTION OF THE PREFERRED EMBODIMENTS

Figure 1:
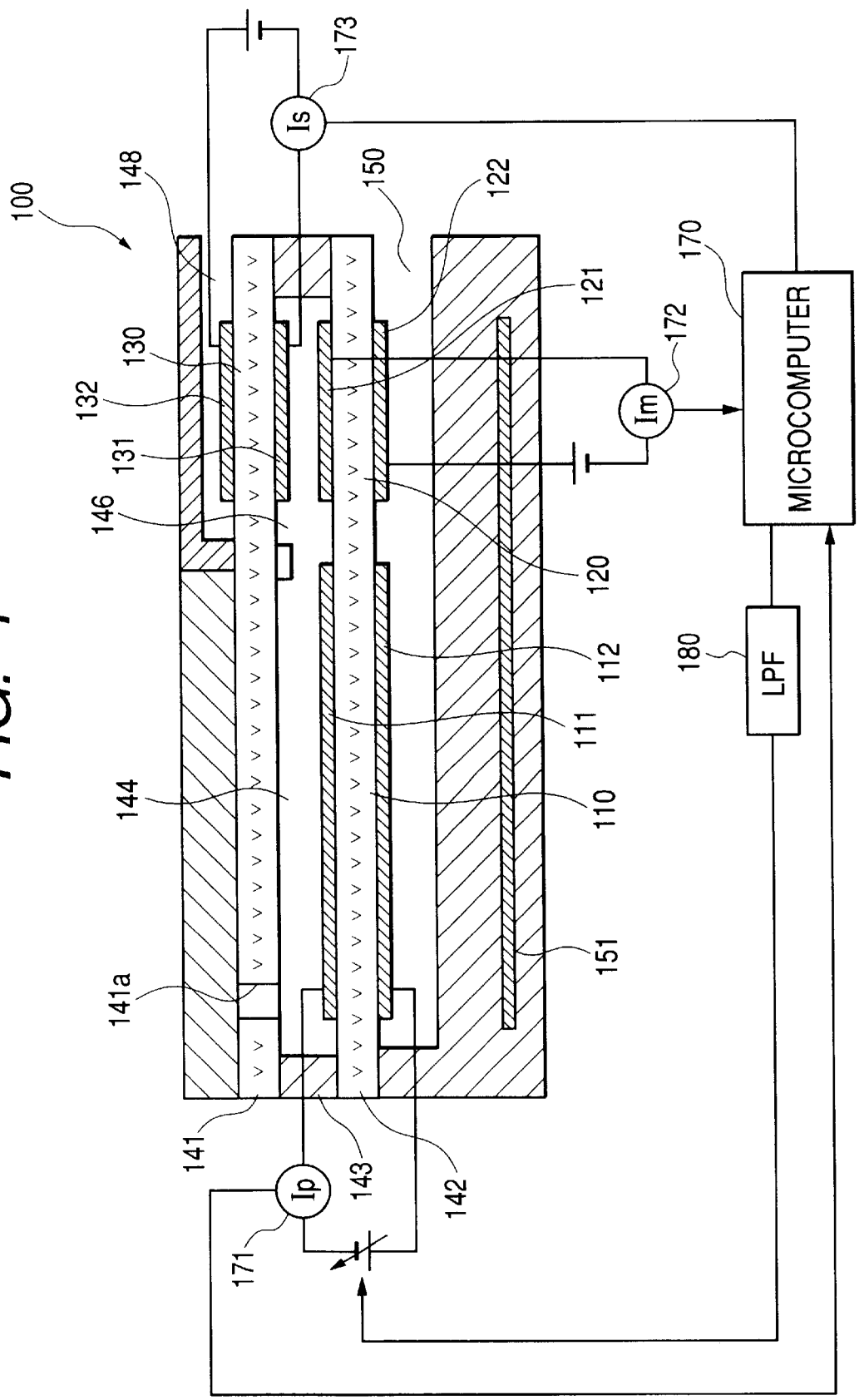
FIG. 1 is a block diagram which shows a gas concentration measuring apparatus according to the first embodiment of the invention.

Referring now to the drawings, wherein like numbers refer to like parts in several views, particularly to FIG. 1, there is shown a gas concentration measuring apparatus according to the first embodiment of the invention which may be used with an automotive control system designed to control the quantity of fuel injected into an internal combustion gasoline engine as a function of an output of the gas concentration measuring apparatus under feedback (F/B) control to bring the air-fuel (A/F) ratio into agreement with a target value. The gas concentration measuring apparatus uses a composite gas sensor capable of measuring concentrations of oxygen ($O_2$) and nitrogen oxide (NOx) contained in exhaust gasses of the internal combustion engine simultaneously.

The gas concentration measuring apparatus, as shown in FIG. 1, generally includes a gas concentration sensor 100, a microcomputer or controller 170, current detectors 171, 172, and 173 (e.g., ammeters), and a low-pass filter 180.

The following discussion will refer to an example in which the gas concentration sensor 100 is installed in an exhaust pipe of an automotive internal combustion engine.

Figure 2:
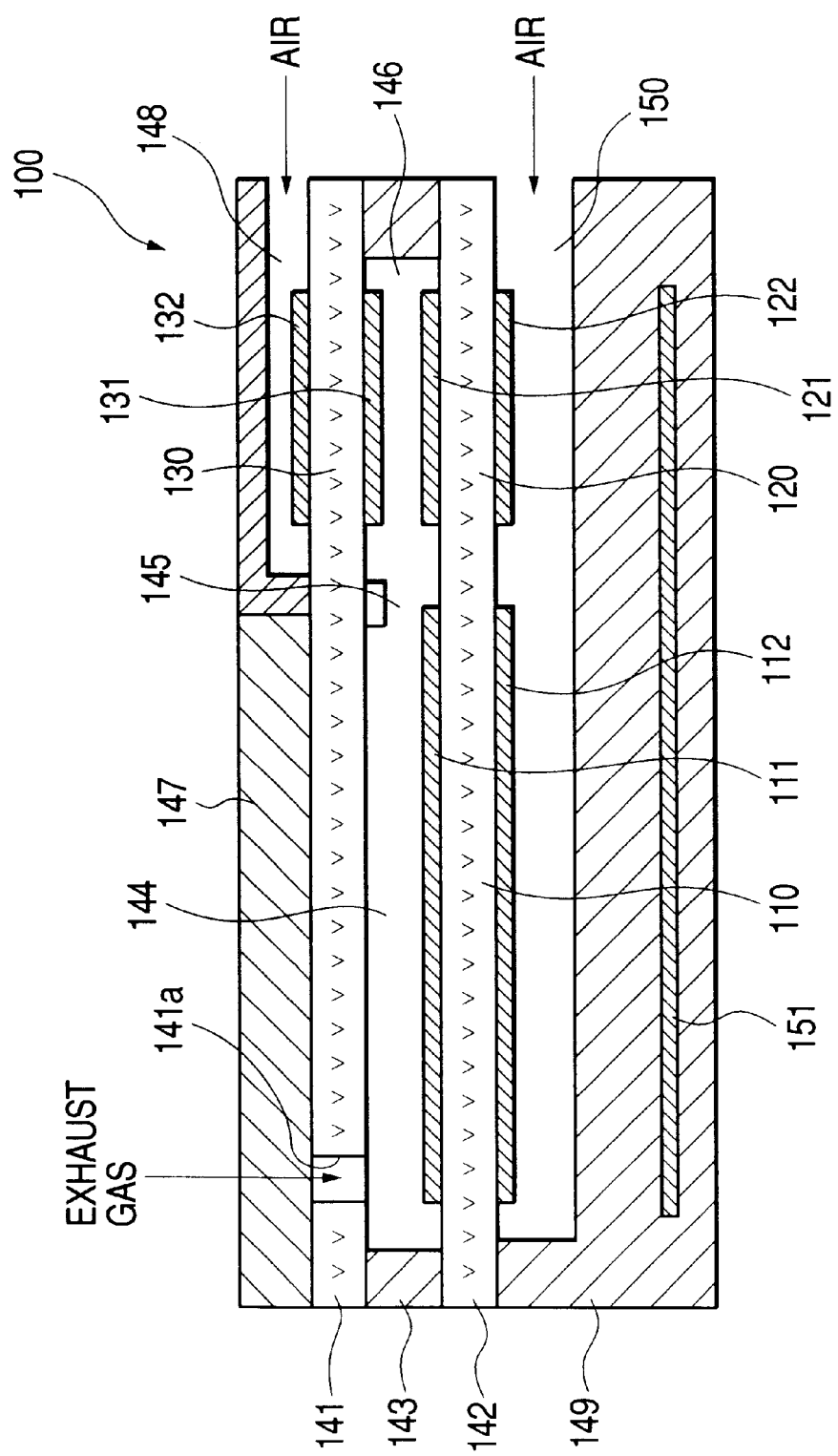
FIG. 2 is a sectional view which shows a gas concentration sensor.

The gas concentration sensor 100 includes generally, as shown in FIG. 2, solid electrolyte plates 141 and 142 made of an oxygen ion-conducting material. The solid electrolyte plates 141 and 142 are laid to overlap each other at a given interval through a spacer 143 made of an insulating material such as alumina. The solid electrolyte plate 141 has formed therein a pinhole 141a through which exhaust gasses flowing around the gas concentration sensor 100 are admitted into a first chamber 144. The first chamber 144 communicates with a second chamber 146 through an orifice 145 working as a diffusion path. On the solid electrolyte plate 141, a porous diffusion layer 147 is formed.

The solid electrolyte plate 142 has formed therein a pump cell 110 and a monitor cell 120. The pump cell 110 works to dissociate or ionize and pump thereinto oxygen molecules ($O_2$) contained the exhaust gasses admitted into the first chamber 144 and discharge them for measuring the concentration of oxygen ($O_2$) contained in the exhaust gasses and also to dissociate or ionize and pump oxygen molecules ($O_2$) within an air passage 150 into the first chamber 144 when the concentration of oxygen within the first chamber 144 is lower than a given level for keeping the concentration of oxygen within the first chamber 144 at the given level. The monitor cell 120 works to produce an electromotive force or current upon application of the voltage as a function the concentration of oxygen ($O_2$) within the second chamber 146. The pump cell 110 has a pair of upper and lower electrodes 111 and 112 disposed on opposed surfaces thereof. The upper electrode 111 is exposed to the first chamber 144 and inactive with respect to NOx, that is, hardly decomposes NOx. Similarly, the monitor cell 120 has a pair of upper and lower electrodes 121 and 122 disposed on opposed surfaces thereof. The upper electrode 121 is exposed to the second chamber 146 and inactive with respect NOx, like the electrode 111. The pump cell 110 and the monitor cell 120 work to pump $O_2$ molecules contained in the exhaust gasses out of the first and second chambers 144 and 146 and discharge them to the air passage 150 through the electrodes 112 and 122.

A sensor cell 130 is formed in the solid electrolyte plate 144 opposite the monitor cell 120 and has a pair of upper and lower electrodes 131 and 132 formed on opposed surfaces thereof. The sensor cell 130 serves to measure the concentration of NOx contained in the exhaust gasses having passed through the pump cell 110 and discharge the oxygen produced when NOx is decomposed within the second chamber 146 to the air passage 148 through the electrode 132.

An insulating layer 149 is disposed on a lower surface, as viewed in FIG. 2, of the solid electrolyte plate 142 to define the air passage 150. The insulating layer 149 has embedded therein a heater 151 for heating the whole of the sensor 100 up to a given temperature.

In operation, when exhaust gasses containing $O_2$, NOx, $CO_2$, and $H_2O$ enter the first chamber 144 through the porous diffusion layer 147 and the pinhole 141a and are passing through the pump cell 110, application of voltage to the pump cell 110 through the electrodes 111 and 112 causes the exhaust gasses to undergo dissociation, so that the oxygen ($O_2$) is pumped into or out of the first chamber 144 as a function of the concentration of oxygen ($O_2$) within the first chamber 144 so as to keep the concentration of oxygen within the first chamber 144 constant. Since the upper electrode 111 of the pump cell 110 is, as described above, made of a metal which hardly decomposes NOx, when the concentration of oxygen within the first chamber 144 is higher than a desired level, only $O_2$ molecules within the first chamber 144 are ionized by the pump cell 110 without decomposing NOx, which are, in turn, discharged to the air passage 150. This causes a current (will also referred to as a pump cell current below) to be produced in the pump cell 11o as a function of the oxygen content of the exhaust gasses. EPO 987 546 A2, assigned to the same assignee as that of this application, teaches control of an operation of this type of gas sensor, disclosure of which is incorporated herein by reference.

The $O_2$ molecules in the exhaust gasses are usually not dissociated by the pump cell 110 completely, so that residual $O_2$ molecules flows into the second chamber 146 and reach the monitor cell 120. The application of given voltage to the monitor cell 120 through the electrodes 121 and 122 causes an output (will also be referred to as a monitor cell current below) to be produced as a function of the concentration of the residual oxygen. The application of given voltage to the sensor cell 130 through the electrodes 131 and 132 causes NOx molecules contained in the exhaust gasses to be decomposed or reduced, so that oxygen ions are produced and discharged to the air passage 148, thereby causing a current (also referred to as a sensor cell current or a NOx current below) to flow through the sensor 130 as a function of the concentration of NOx within the second chamber 146.

Figure 3A:
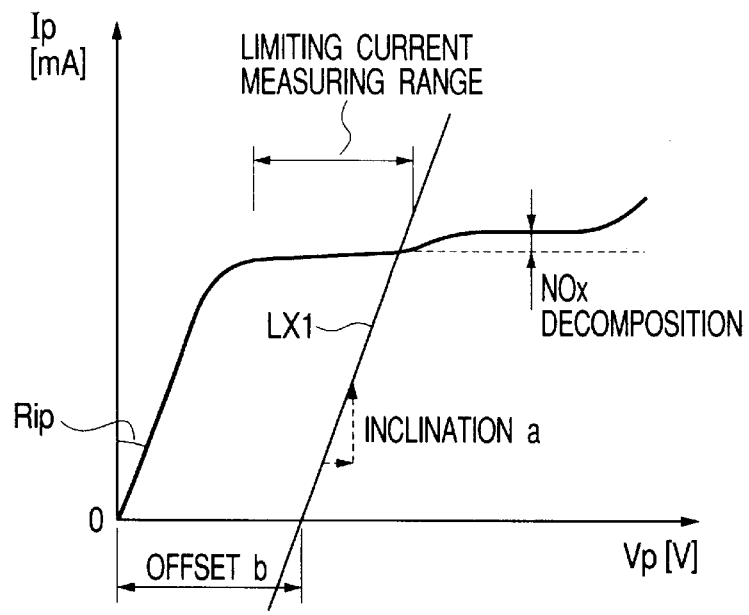
FIG. 3(*a*) shows an example of a map listing an applied voltage-to-output current relation of a pump cell.
Figure 3B:
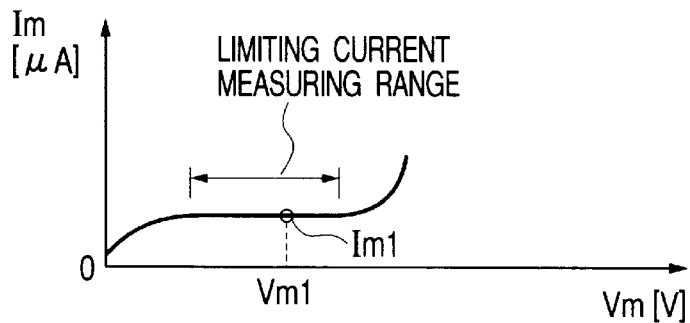
Figure 3C:
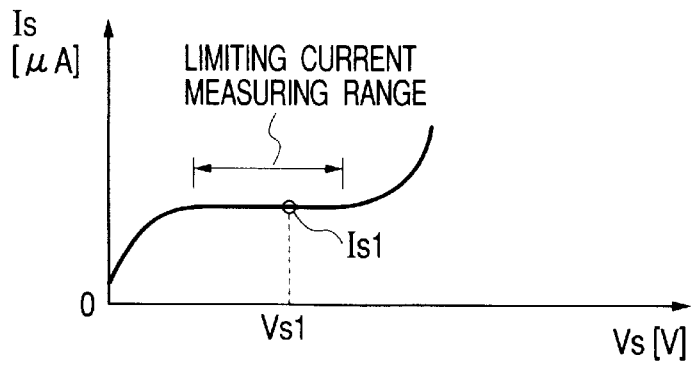

FIGS. 3(a), 3(b), and 3(c) show examples of V-I relations between the voltages applied to the pump cell 110, the monitor cell 120, and the sensor cell 130 and outputs thereof: the pump cell current, the monitor cell current, and the sensor cell current, respectively. Note that FIGS. 3(a) to 3(c) illustrate sensor output characteristics when the concentration of $O_2$ and NOx are constant.

The pump cell 110 works to produce a limiting current as a function of the concentration of oxygen ($O_2$) within the first chamber 144. A straight segment of a curve, as shown in FIG. 3(a), inclined slightly upward with respect to a V-axis (i.e., abscissa axis) indicates a limiting current measuring range in which the limiting current produced by the pump cell 110 is to be measured. The limiting current measuring range is shifted to the positive side of voltage applied to the pump cell 110 as the concentration of oxygen increases. This limiting current characteristics has a resistance-dependent range defined by a segment of the curve extending upward at an inclination substantially depending upon an impedance Rip of the pump cell 110 (i.e., the solid electrolyte plate 142).

The gas concentration measuring apparatus of this embodiment stores therein a V-I map such as the one of FIG. 3(a) and monitors the pump cell current Ip to determine the pump cell-applied voltage Vp to be applied to the pump cell 110 by look-up using the V-I map. The V-I map has a target applying voltage line LX1 defined by an inclination a and an offset b and is used in determining the pump cell-applied voltage Vp along the line LX1. The upper pump cell electrode 111 of the pump cell 110 exposed to the first chamber 144 is, as described above, made of material which hardly decomposes NOx, so that NOx molecules in the exhaust gasses are hardly decomposed, but if the voltage applied to the pump cell 110 exceeds a certain upper limit, it will cause the NOx molecules to be decomposed, thereby producing an error in the pump cell current Ip (i.e., the limiting current) outputted from the pump cell 110. In practice, the target applying voltage line LX1 is so defined as to keep the concentration of oxygen ($O_2$) within the first chamber 144 at a lower level (near the stoichiometric). For instance, the target applying voltage line LX1 is so defined that a small quantity of $O_2$ (e.g., several ppm to several tens ppm) remains in the first chamber 144.

The monitor cell 120, like the pump cell 110, works to produce a limiting current as a function of the concentration of oxygen ($O_2$) within the second chamber 146. The application of a given voltage Vm1, as shown in FIG. 3(b), to the monitor cell 120 causes a current Im1 to be produced. When the concentration of oxygen within the second chamber 146 is also kept at a lower level, e.g., several ppm to several tens ppm, by the activity of the pump cell 110, the monitor cell 120 produces a monitor cell current Im of the order of 0.5 to 2 $\mu$A.

The sensor cell 130 works to produce a limiting current as a function of the concentration of NOx. Specifically, the sensor cell 130 provides an output as a function of the concentration of NOx contained in the gasses within the second chamber 146. The application of a given voltage Vs1, as shown in FIG. 3(c), to the sensor cell 130 causes a current Is1 to be produced.

Returning back to FIG. 1, the microcomputer 170 is implemented by a typical arithmetic logic unit consisting of a CPU, a memory, an A/D converter, a D/A converter, etc.

Power supply circuits are, as clearly shown in the drawing, provided one for each of the pump cell 110, the monitor cell 120, and the sensor cell 130. The power supply circuits include voltage sources for applying the voltages Vp, Vm, and Vs to the pump cell 110, the monitor cell 120, and the sensor cell 130 and the current detectors 171, 172, and 173, respectively. The current detector 171 measures the pump cell current Ip produced by the pump cell 110 and provides a signal indicative thereof to the microcomputer 170. The current detector 172 measures the monitor cell current Im produced by the monitor cell 120 and provides a signal indicative thereof to the microcomputer 170. The current detector 173 measures the sensor cell current Is produced by the sensor cell 130 and provides a signal indicative thereof to the microcomputer 170.

The microcomputer 170 receives the output from the current detector 171 of the pump cell 110 indicative of the pump cell current Ip and determines the concentration of oxygen ($O_2$) in the exhaust gasses and the pump cell-applied voltage Vp to be applied to the pump cell 110 using the target applying voltage line LX1 in the map of FIG. 3(a). The pump cell-applied voltage Vp is selected so as not to decompose NOx through the pump cell 110. Further, the microcomputer 170 corrects the pump cell-applied voltage characteristics using the monitor cell current Im measured by the current detector 172 and determines the concentration of NOx using the sensor cell current Is measured by the current detector 173.

The microcomputer 170 measures the impedance of the pump cell 110 using the sweep method. The measurement of the impedance is achieved by changing the pump cell-applied voltage Vp to either of positive and negative sides instantaneously to produce an ac voltage which is, in turn, blurred in the form of a sine wave through the low-pass filter 180 and applied to the pump cell 110. The frequency of the ac voltage is preferably higher than 10 KHz. The time constant of the low-pass filter 180 is in the order of 5 μsec. The microcomputer 170 monitors changes in the voltage and the pump cell current Ip to calculate the impedance of the pump cell 110. The low-pass filter 180 may be implemented by a primary filter consisting of a resistor and capacitor.

Figure 4:
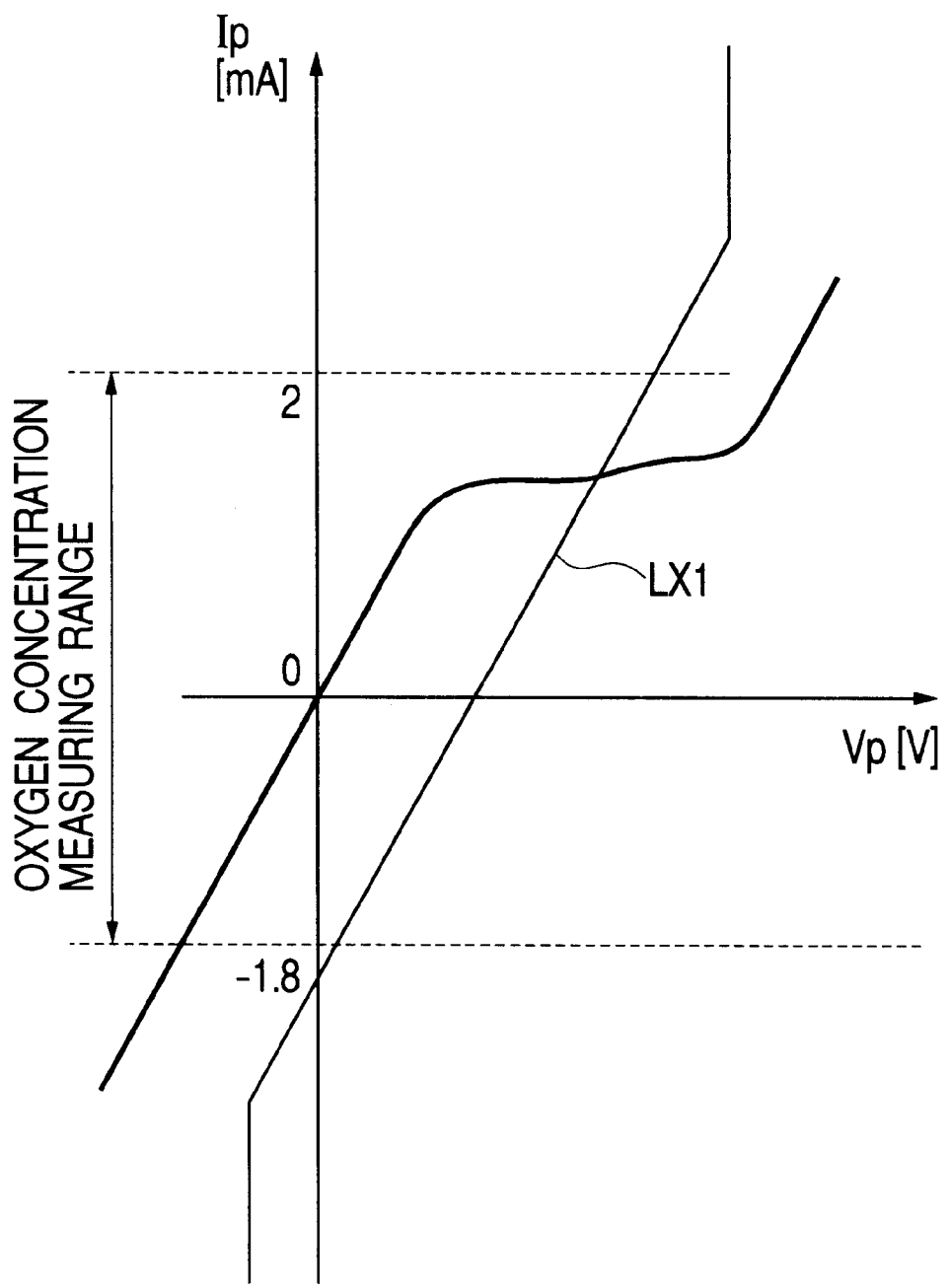
FIG. 4 is an example of an applied voltage-to-output current map stored in a microcomputer for determining a target voltage to be applied to a pump cell.

The microcomputer 170 sets a current measuring range in which the pump cell current Ip is to be measured. The current measuring range is defined as an oxygen concentration measuring range in the V-I map for the pump cell 110 as shown in FIG. 4. In the illustrated example, the oxygen concentration measuring range is defined between Ip=−1.8 mA and Ip=2 mA. The target applying voltage line LX1 is so determined that the pump cell-applied voltage Vp is controlled variably at least within the oxygen concentration measuring range. The microcomputer 170 stores the target applying voltage line LX1 in the memory as map data. Within ranges other than the oxygen concentration measuring range, it is unnecessary to change the pump cell-applied voltage Vp, and, thus, the target applying voltage line LX1 has segments extending straight vertically.

The correction of the pump cell-applied voltage characteristics using the monitor cell current Im will be described below in detail with reference to FIGS. 5(a), 5(b), and 5(c). Note that FIGS. 5(a) to 5(c) show examples of the applied voltage characteristics or V-I relations between voltages applied to the pump cell 110, the monitor cell 120, and the sensor cell 130 and outputs thereof when the concentration of $O_2$ and NOx are, like the FIGS. 3(a) to 3(c), constant and that solid lines (1) denote the reference V-I curves in FIGS. 3(a), 3(b), and 3(c), respectively.

Figure 5A:
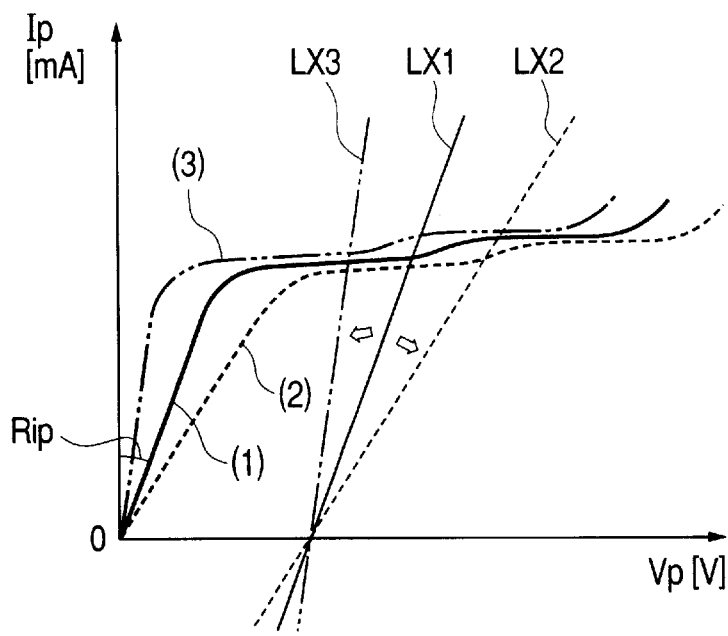
FIG. 5(*a*) is a map showing a variation in applied voltage-to-output current relation of a pump cell with a variation in impedance of a pump cell which is used to correct the voltage to be applied to the pump cell as a function of the impedance of the pump cell.
Figure 5B:
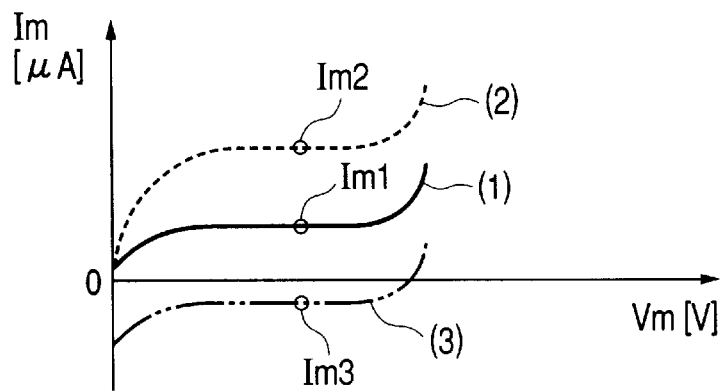
Figure 5C:
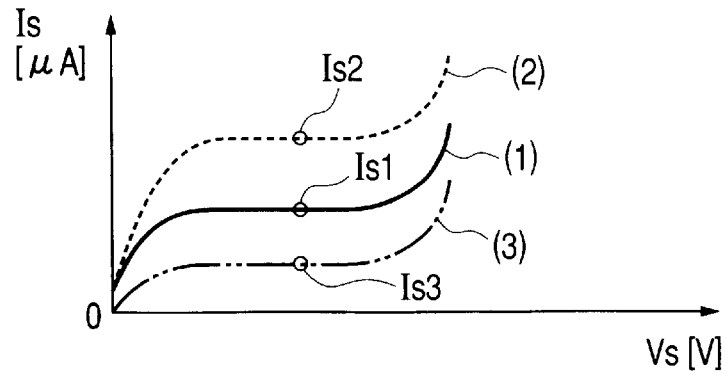

When the impedance Rip of the pump cell 110 is increased with a drop in temperature of exhaust gasses or greater than a reference value due to an inherent error of the pump cell 110, it will cause the V-I relation, as expressed by the solid line (1) in FIG. 5(a), to be shifted to a broken line (2), thereby making it impossible to dissociate $O_2$ molecules sufficiently by application of the pump cell-applied voltage Vp determined by the target applying voltage line LX1 to the pump cell 110. This phenomenon is attributed to the slightly upward inclination of the segment of the V-I curve within the limiting current measuring range. Specifically, as the V-I curve is inclined to the right like the broken line (2), an undissociated quantity of $O_2$ increases. This causes residual $O_2$ within the first and second chambers 144 and 146 to increase, thereby resulting in, as shown in FIG. 5(b), a change in the V-I relation of the monitor cell 120 from the solid line (1) to a broken line (2) (i.e., a change in monitor cell current from Im1 to Im2). Additionally, the quantity of $O_2$ to be dissociated by the sensor cell 130 together with NOx also increases, thereby causing the V-I relation of the sensor cell 130, as shown in FIG. 5(c), to be changed from the solid line (1) to a broken line (2), which leads to an error in determining the concentration of NOx (=Is2−Is1).

Conversely, when the impedance Rip of the pump cell 110 is decreased with a rise in temperature of exhaust gasses or lower than the reference value due to an inherent error of the pump cell 110, it will cause the V-I relation, as expressed by the solid line (1) in FIG. 5(a), to be shifted to a two-dot chain line (3), thereby resulting in dissociation of a portion of NOx molecules as well as all $O_2$ molecules within the first chamber 144 when the pump cell-applied voltage Vp determined by the target applying voltage line LX1 is applied to the pump cell 110. This causes the V-I relation of the monitor cell 120 to be changed from the solid line (1) to a two-dot chain line (3) (i.e., a change in monitor cell current from Im1 to Im3). Additionally, since the portion of the NOx molecules has been already dissociated by the pump cell 110, the V-I relation of the sensor cell 130, as shown in FIG. 5(c), to be changed from the solid line (1) to a two-dot chain line (3), which leads to an error in determining the concentration of NOx (=Is3−Is1)

Specifically, a change in impedance Rip of the pump cell 110 will cause the residual quantity of $O_2$ within the first and second chambers 144 and 146 to change, which results in an error in determining the concentration of NOx. In order to avoid this problem, the gas concentration measuring apparatus of this embodiment determines a change in residual quantity of $O_2$ based on the monitor cell current Im produced by the monitor cell 120 to correct the pump cell-applied voltage Vp to be applied to the pump cell 110.

When the impedance Rip of the pump cell 110 is increased, resulting in an increase in residual quantity of $O_2$, the quantity of $O_2$ the pump cell 110 dissociates needs to be increased. The microcomputer 170 detects such a condition from the monitor cell current Im2 and changes the target applying voltage line Lx1 to LX2 in FIG. 5(a). The inclination of the line LX2 is smaller than that of the line LX1, so that the pump cell-applied voltage Vp is so corrected as to increase in level. This results in a decrease in residual quantity of $O_2$ within the first and second chambers 144 and 146 to a desired one, so that the monitor cell 120 and the sensor cell 130 will have the V-I relations, as indicated by the solid lines (1) in FIGS. 5(b) and 5(c), respectively, thereby eliminating the error in determining the concentration of NOx.

Alternatively, when the impedance Rip of the pump cell 110 is decreased, so that the pump cell 110 dissociates or decomposes NOx undesirably, the quantity of $O_2$ the pump cell 110 dissociates needs to be decreased. The microcomputer 170 detects such a condition from the monitor cell current Im3 and changes the target applying voltage line LX1 to LX3 in FIG. 5(a). The inclination of the line LX3 is greater than that of the line LX1, so that the pump cell-applied voltage Vp is so corrected as to decrease in level. This results in an increase in residual quantity of $O_2$ within the first and second chambers 144 and 146 to a desired one, so that the monitor cell 120 and the sensor cell 130 will have the V-I relations, as indicated by the solid lines (1) in FIGS. 5(b) and 5(c), respectively, thereby eliminating the error in determining the concentration of NOx.

Figure 6:
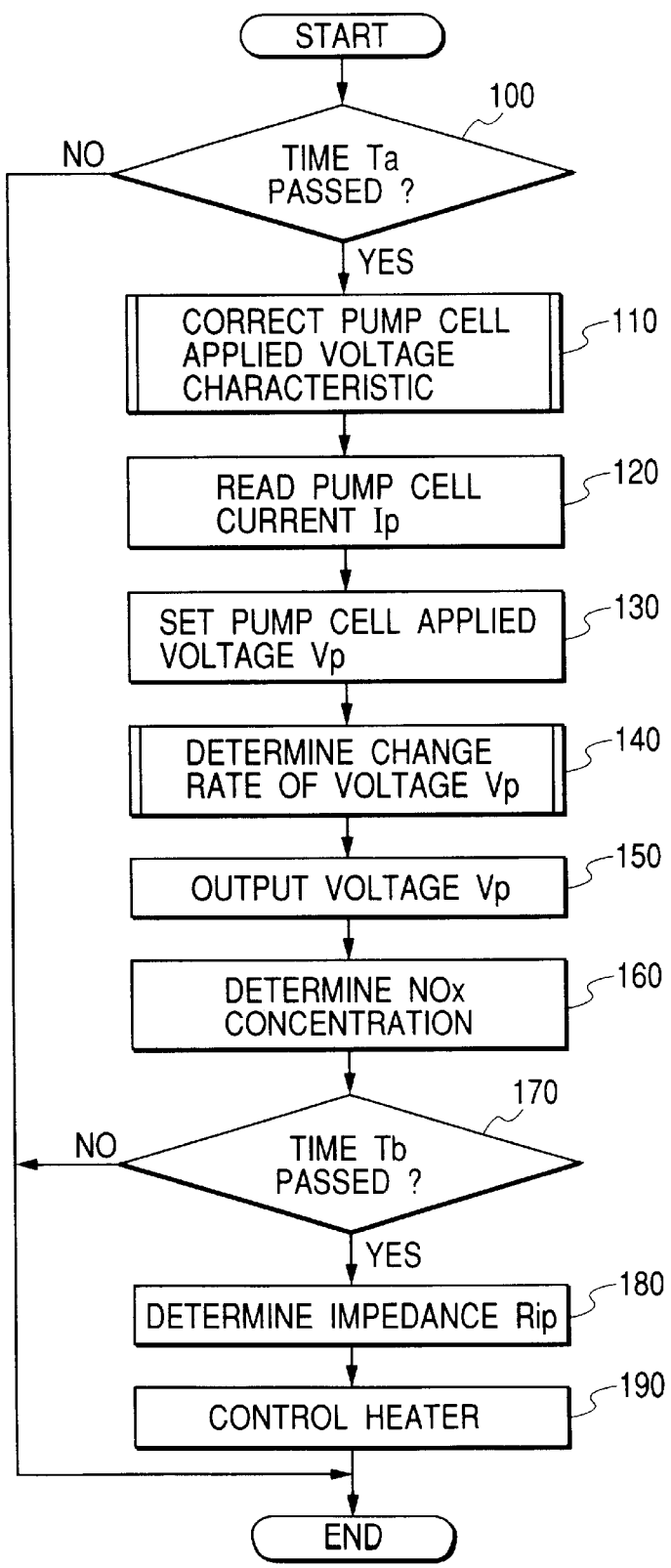
FIG. 6 is a flowchart of a main program to control an operation of a gas concentration measuring apparatus according to the first embodiment of the invention.

FIG. 6 shows a flowchart of a program or logical steps performed by the microcomputer 170 to determine the pump cell-applied voltage Vp.

Upon turning on of the microcomputer 170, the routine enters the program and proceeds to step 100 wherein it is determined whether a preselected period of time Ta has elapsed after the concentrations of $O_2$ and NOx are measured in a previous cycle or not. The time Ta is, for example, 4 msec. that is equivalent to one cycle of measurement of the concentrations of $O_2$ and NOx.

If a YES answer is obtained in step 100, then the routine proceeds to step 110 wherein the monitor cell current Im is monitored to correct the pump cell-applied voltage Vp to be applied to the pump cell 110 by shifting the target applying voltage line LX1 as described above. This correction will be discussed later in detail with reference to FIG. 7.

The routine proceeds to step 120 wherein the pump cell current Ip is read out of the current detector 171. The routine proceeds to step 130 wherein the pump cell-applied voltage Vp is determined as a function of the pump cell current Ip using the target applying voltage line LX1 corrected in step 110.

The routine proceeds to step 140 wherein the rate at which the pump cell-applied voltage Vp is to be changed is determined. This determination will be described later in detail with reference to FIG. 8.

The routine proceeds to step 150 wherein the pump cell-applied voltage Vp determined in step 130 is outputted to the pump cell 110 at the rate set in step 140. The routine proceeds to step 160 wherein after the pump cell current Ip is in a steady state following application of the pump cell-applied voltage Vp, the concentration of oxygen ($O_2$) contained in the exhaust gasses (or an air-fuel ratio) is determined as a function of the pump cell current Ip. The concentration of NOx contained in the exhaust gasses is also determined as a function of the sensor cell current Is. Note that the microcomputer 170 outputs the sensor cell-applied voltage Vs of a constant level to the sensor cell 130 at all times.

The routine proceeds to step 170 wherein it is determined whether a preselected period of time Tb has elapsed after previous determination of the impedance Rip of the pump cell 110 or not. The time Tb is equivalent to one cycle of measurement of the impedance Rip and selected, for example, from 128 msec. and 2 sec. depending upon operating conditions of the engine. If a NO answer is obtained in step 170, then the routine terminates. Alternatively, if a YES answer is obtained, then the routine proceeds to step 180 wherein the impedance Rip is determined and updated. The routine proceeds to step 190 wherein the current to be applied to the heater 151 is controlled in a manner, as will be described below in detail.

The measurement of the impedance Rip of the pump cell 110 in step 180 is accomplished by changing the pump cell-applied voltage Vp to either of positive and negative sides of the monitor cell-applied voltage Vm instantaneously for several tens μsec. to 100 μsec. and monitoring a change in the pump cell-applied voltage Vp and a change in the pump cell current Ip to calculate the impedance Rip of the pump cell 110 (Rip=the change in the pump cell-applied voltage Vp /the change in the pump cell current Ip).

The control of the current to be applied to the heater 151 is achieved by adjusting the current so as to bring the impedance Rip into agreement with a target one. For example, when the temperature of the gas concentration sensor 100 is lower than a given threshold value, and the impedance Rip is higher, the heater 151 is energized at a controlled duty cycle of 100%. When the temperature of the gas concentration sensor 100 rises above the threshold value, the duty cycle is changed using the known PID control techniques, and the heater 151 is energized at the changed duty cycle.

Figure 7:
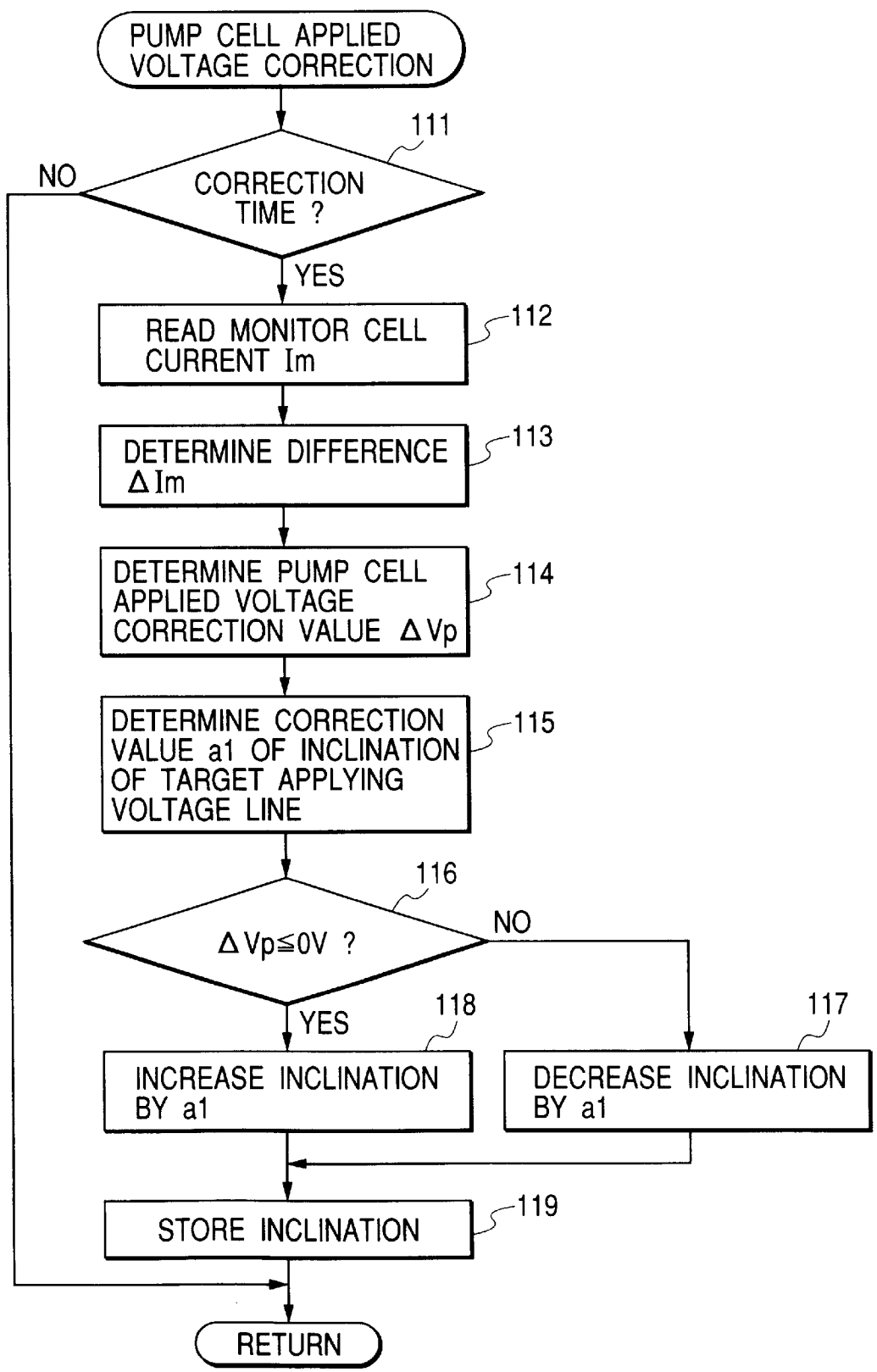
FIG. 7 is a flowchart of a program to correct the voltage to be applied to a pump cell.

FIG. 7 is a flowchart of a program performed in step 110 of FIG. 6 to correct the pump cell-applied voltage Vp.

After entering the program, the routine proceeds to step 111 wherein it is determined whether a correction time when the pump cell-applied voltage Vp should be corrected has been reached or not. For example, the correction time is set to an interval of 10 to several hundreds msec.

If a YES answer is obtained in step 111, then the routine proceeds to step 112 wherein the monitor cell current Im is read out of the current detector 172. The routine proceeds to step 113 wherein a difference between the monitor cell current Im derived in step 112 and a target monitor cell current Imtg is determined as a current difference ΔIm (Imtg−Im). The target monitor cell current Imtg is set to, for example, 0.5 to 2 μA required for keeping the concentration of oxygen within the second chamber 146 at a given low oxygen level (e.g., near the stoichiometric).

The routine proceeds to step 114 wherein a correction value ΔVP of the pump cell-applied voltage Vp is determined as a function of the current difference ΔIm. The correction value ΔVP is an increment or a decrement of the pump cell-applied voltage Vp required for eliminating the current difference ΔIm. Specifically, when an actual value of the monitor cell current Im is greater than the target monitor cell current Imtg (i.e., ΔIm<0), the correction value ΔVP is so determined as to increment the pump cell-applied voltage Vp. Alternatively, when an actual value of the monitor cell current Im is smaller than the target monitor cell current Imtg (i.e., ΔIm>0), the correction value ΔVP is so determined as to decrement the pump cell-applied voltage Vp.

The routine proceeds to step 115 wherein a correction value a1 of the inclination of the target applying voltage line LX1 is determined based on the correction value ΔVP derived in step 114. The correction value a1 is set substantially proportional to the correction value ΔVP. The routine proceeds to step 116 wherein it is determined whether the correction value ΔVP is positive or negative. If a YES answer is obtained meaning that the correction value ΔVP is positive, then the routine proceeds to step 117 wherein the inclination of the target applying voltage line LX1 is decreased by the correction value a1. Alternatively, if a NO answer is obtained meaning that the correction value ΔVP is negative, then the routine proceeds to step 118 wherein the inclination of the target applying voltage line LX1 is increased by the correction value a1. The routine proceeds to step 119 wherein the corrected inclination of the target applying voltage line LX1 is stored in the memory of the microcomputer 170.

Specifically, in step 117, the target applying voltage line LX1 of the V-I map, for example, in FIG. 5(*a*) is changed to LX2, thereby correcting the pump cell-applied voltage Vp in a direction in which the residual quantity of $O_2$ within the first chamber 144 is decreased. In step 118, the target applying voltage line LX1 of the V-I map, for example, in FIG. 5(*a*) is changed to LX3, thereby correcting the pump cell-applied voltage Vp in a direction in which the residual quantity of $O_2$ within the first chamber 144 is increased. In other words, steps 117 and 118 work to bring the monitor cell current Im into agreement with the target monitor cell current Imtg (=Im1 in FIG. 5(*b*)), thereby keeping the concentration of oxygen constant in the first and second chambers 144 and 146.

After the pump cell-applied voltage characteristics or the V-I map is corrected in the above manner, the microcomputer 170 determines the pump cell-applied voltage Vp as a function of the pump cell current Ip using the corrected V-I map (i.e., the target voltage applying line LX1) in a cycle (e.g., 4 msec.) shorter than a cycle of the correction of the V-I map (e.g., 10 to several hundreds msec.).

Figure 8:
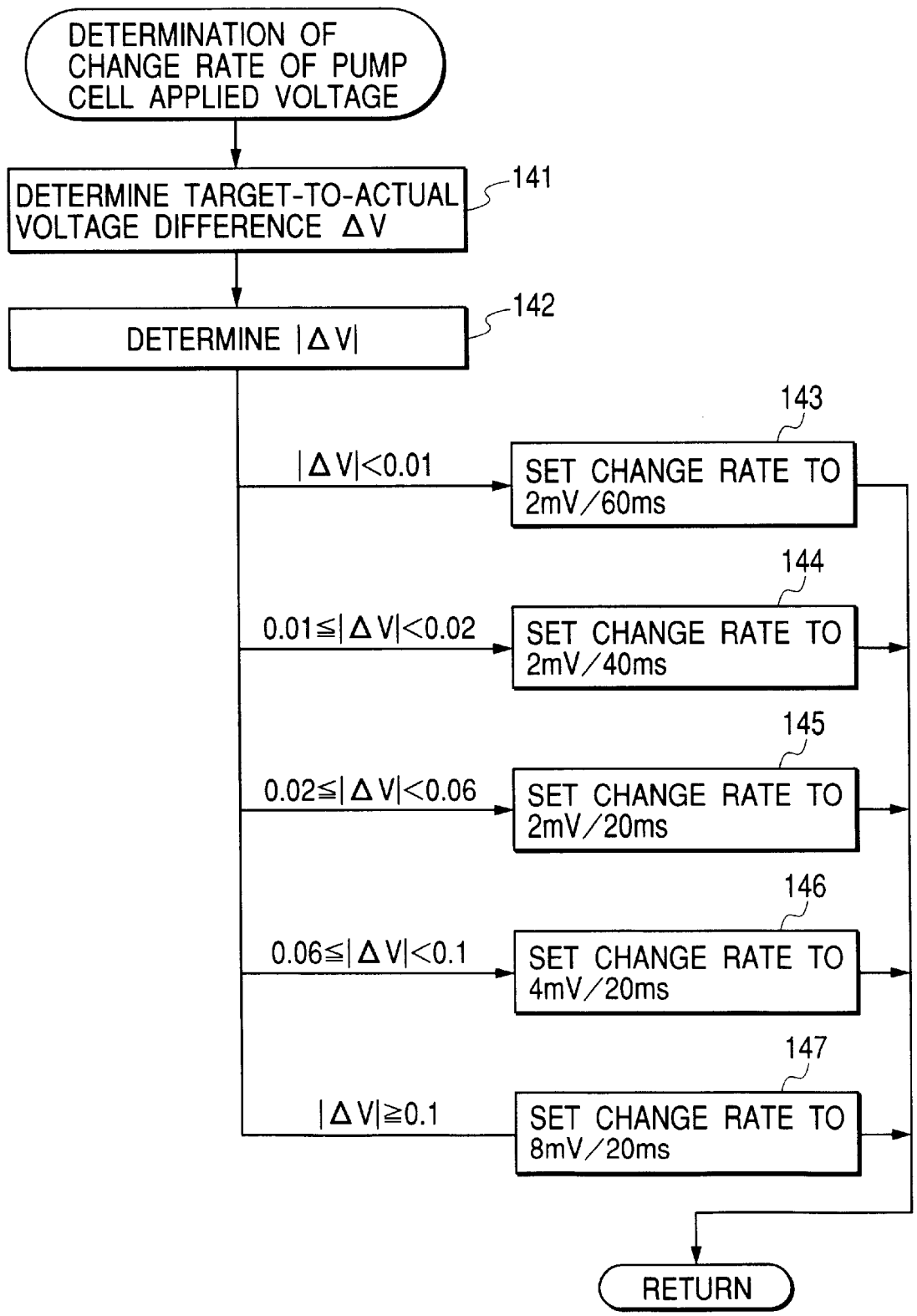
FIG. 8 is a flowchart of a program to determine a rate at which the voltage applied to a pump cell is to be changed.

FIG. 8 is a flowchart of a program performed in step 140 of FIG. 6 to determine the rate at which the pump cell-applied voltage Vp is to be changed.

After entering the program, the routine proceeds to step 141 wherein a difference between the pump cell-applied voltage Vp determined in step 130 of FIG. 6, that is, a target voltage to be applied to the pump cell 110 and an actual voltage being now applied to the pump cell 110 is determined as a voltage difference ΔV.

The routine proceeds to step 142 wherein an absolute value of the voltage difference ΔV is determined. Subsequent steps 143, 144, 145, 146, and 147 each determine the change rate of the pump cell-applied voltage Vp as a function of the voltage difference ΔV. Specifically, after determination of the absolute value of the voltage difference ΔV, step 142 also determines which of preselected ranges the absolute value of the voltage difference ΔV falls. As the absolute value of the voltage difference ΔV increases, the change rate of the pump cell-applied voltage Vp is set to a greater value. Additionally, as the voltage difference ΔV decreases, a cycle in which the pump cell-applied voltage Vp is changed is also prolonged.

Figure 9:
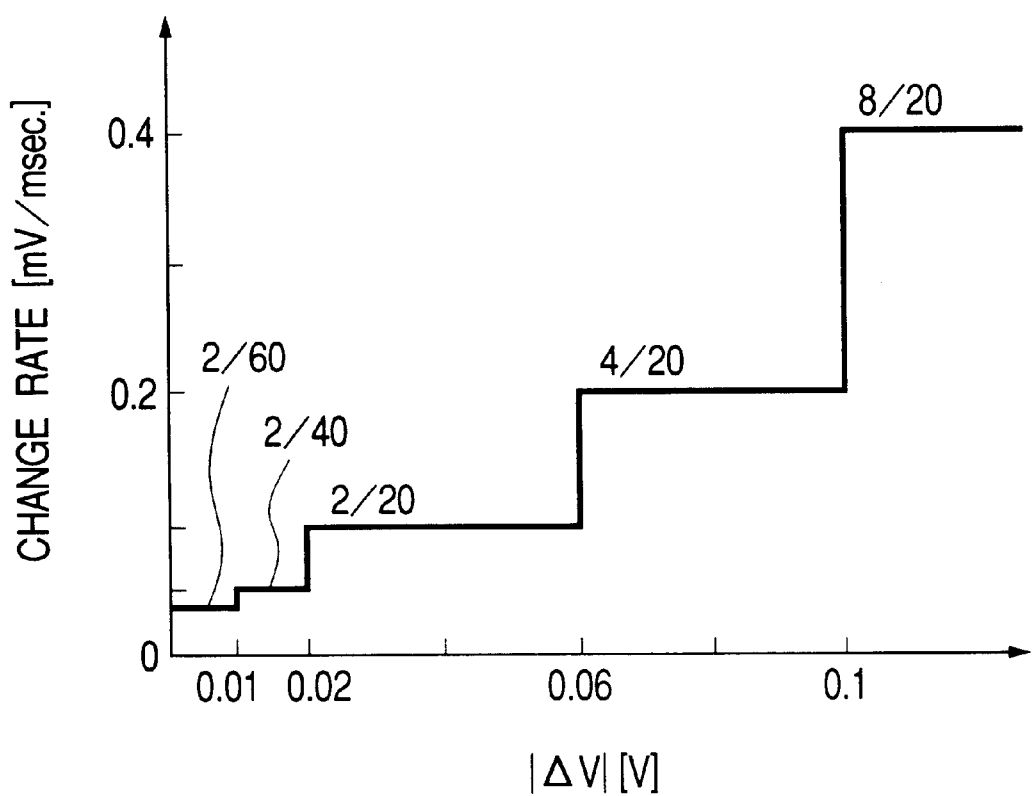
FIG. 9 shows a relation between a rate at which the voltage applied to a pump cell is to be changed and a difference between a target voltage to be applied to the pump cell and an actual voltage being applied to the pump cell.

The operations of steps 142 to 147 will be described below in more detail with reference to FIGS. 8 and 9.

Step 142 determines which range the absolute value of the voltage difference ΔV falls. If the absolute value of the voltage difference ΔV falls within a range of less than 0.01, then the routine proceeds to step 143 wherein the change rate is set to 2 mV/60 msec. If the absolute value of the voltage difference ΔV falls within a range of 0.01 to 0.02, then the routine proceeds to step 144 wherein the change rate is set to 2 mV/40 msec. If the absolute value of the voltage difference ΔV falls within a range of 0.02 to 0.06, then the routine proceeds to step 145 wherein the change rate is set to 2 mV/20 msec. If the absolute value of the voltage difference ΔV falls within a range of 0.06 to 0.1, then the routine proceeds to step 146 wherein the change rate is set to 4 mV/20 msec. If the absolute value of the voltage difference ΔV falls within a range of 0.1 or more, then the routine proceeds to step 146 wherein the change rate is set to 8 mV/20 msec. Each value, as illustrated in FIGS. 8 and 9, is merely an example and may be set to another. It is advisable that the change rate, as can be seen from FIG. 9, be increased as the absolute value of the voltage difference ΔV is increased.

As apparent from the above discussion, unlike conventional systems in which a monitor cell electromotive force is brought into agreement with a target one under feedback control, the gas concentration measuring apparatus of this embodiment is designed to control the pump cell-applied voltage Vp to be applied to the pump cell 110 using the V-I map stored in the memory, thereby avoiding undesirable oscillation of an applied voltage control circuit for the pump cell 110 which contributes to a great change in residual quantity of $O_2$ within the first and second chambers 144 and 146, thereby eliminating the error in determining the concentration of NOx.

Figure 22A:
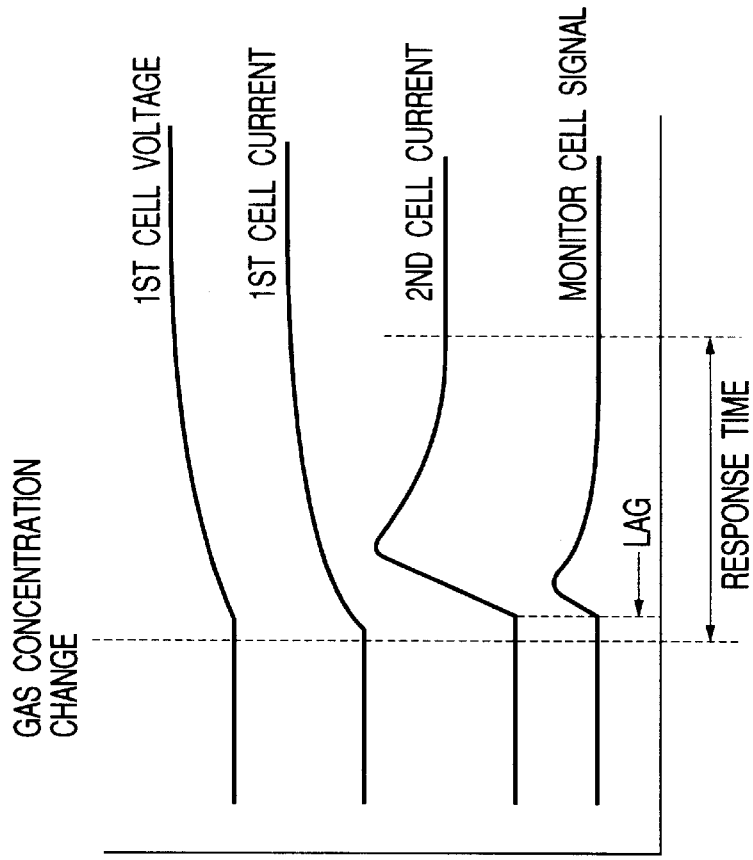
FIG. 22(a) is a time chart showing changes in voltage to be applied to a pump cell and outputs of the pump cell, a monitor cell, and a sensor cell in a gas concentration measuring apparatus of the invention.
Figure 22B:
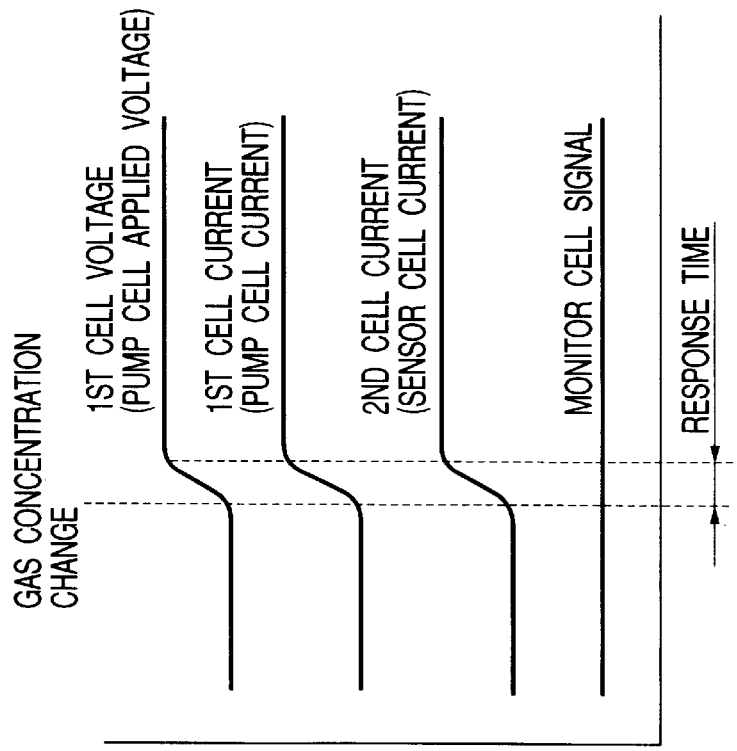
FIG. 22(b) is a time chart showing changes in voltage to be applied to a pump cell and outputs of the pump cell, a monitor cell, and a sensor cell in a conventional gas concentration measuring apparatus.

Additionally, when the pump cell current Ip changes, as shown in FIG. 22(a), during change in concentration of NOx, the pump cell-applied voltage Vp is adjusted to a target one immediately following the change in pump cell current Ip. This avoids an undesirable increase in residual quantity of $O_2$ within the first and second chambers 144 and 146, thereby avoiding an unwanted change in monitor cell current Im, which enables the sensor cell 130 to produce the sensor cell current Is indicative of the concentration of NOx accurately at a quick response.

The response delay of the monitor cell 120 increases, especially in the structure in which the first chamber 144 communicates with the second chamber 146 through the orifice 145. Such a problem may, however, be alleviated by the gas concentration measuring apparatus of this embodiment.

A target voltage to be applied to the pump cell 110 is, as described above, corrected as a function of the monitor cell current Im produced by the monitor cell 120, so that the residual quantity of $O_2$ within the first and second chambers 144 and 146 is optimized. Specifically, the monitor cell current Im is converged on a target one, so that the residual quantity of $O_2$ within the first and second chambers 144 and 146 is kept at a desired level. Therefore, even if the activity of the pump cell 110 changes due to a change in temperature of exhaust gasses arising from rapid acceleration or deceleration of the engine, an inherent error, or deterioration of the pump cell 110, the gas concentration measuring apparatus of this embodiment is capable of measuring the concentration of NOx with high accuracy.

The correction of the V-I map for the pump cell 110 is, as described above, executed in a cycle of, for example, 10 to several hundreds msec. longer than that (e.g., 4 msec.) of control of the pump cell-applied voltage Vp. Specifically, such a correction is executed in a cycle determined by taking into consideration a change in response of the gas concentration sensor 100 due to deterioration or inherent error thereof, thereby minimizing undesirable oscillations of the control circuit during control of the applied voltage.

The change rate of the pump cell-applied voltage Vp is, as described above, controlled variably, thereby allowing the activity of the pump cell 110 to pump the residual $O_2$ out of the first chamber 144 or pump $O_2$ into the first chamber 144 to be enhanced, which results in improved NOx measurement response and accuracy. Particularly, when the voltage difference ΔV between the pump cell-applied voltage Vp and an actual voltage being applied to the pump cell 110 is relatively small, the cycle in which the pump cell-applied voltage Vp is change is prolonged, thereby eliminating the effect of a peak current during the change in pump cell-applied voltage Vp. Specifically, the change in Vp usually causes a peak (i.e., tailing) of the pump cell current Ip to be produced, but in this embodiment, the pump cell-applied voltage Vp is changed after the peak of the pump cell current Ip disappears, thereby resulting in improved reliability of control of the pump cell-applied voltage Vp.

Figure 10:
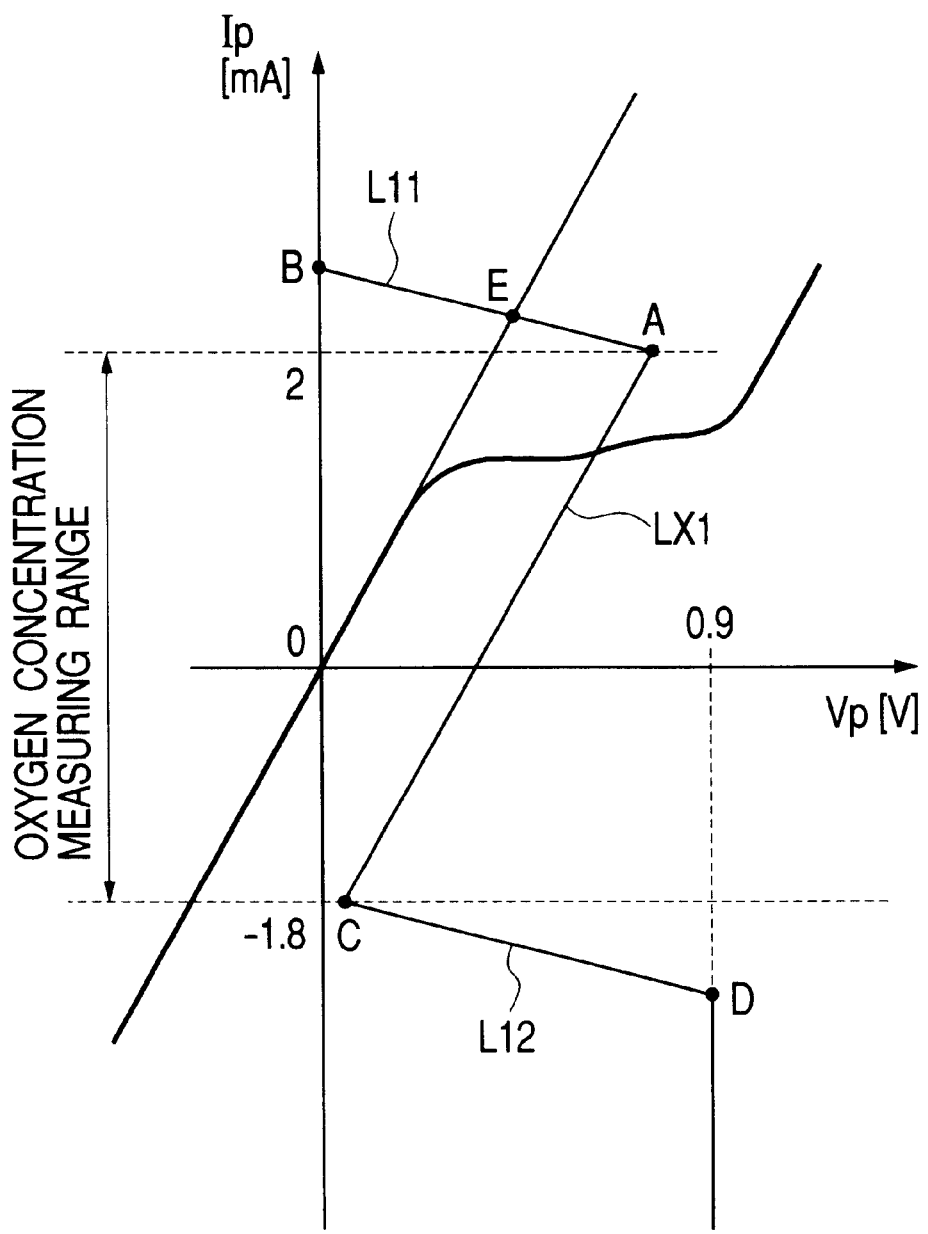
FIG. 10 shows a modification of the one shown in FIG. 4.

As the V-I map for use in determining the pump cell-applied voltage Vp, one as shown in FIG. 10 may be employed. In this map, the target applying voltage line LX1 is, like the above embodiment, defined within an oxygen concentration measuring range, and additional target applying voltage lines L11 and L12 are defined on lean and rich sides of the oxygen concentration measuring range, respectively. The target applying voltage line L11 is a primary line extending between a point A that is a lean limit of the oxygen concentration measuring range and a point B defined on an ordinate axis indicating Vp=0 (electromotive force on the lean side). The target applying voltage line L12 is a primary line extending between a point C that is a rich limit of the oxygen concentration measuring range and a point D defined on a vertical line indicating Vp=0.9 V (electromotive force on the rich side). Specifically, the target applying voltage line LX1 has substantially the same inclination as that of a resistance-dependent portion of a V-I curve (i.e., a rising portion of the V-I curve defined by the impedance of the pump cell 110), while the target applying voltage lines LX11 and LX12 have inclinations reverse in sign to the target applying voltage line LX1.

The use of the V-I map of FIG. 10 prevents the pump cell current Ip from increasing undesirably outside the oxygen concentration measuring range by means of the target applying voltage lines LX11 and LX12. Specifically, even if the sensor 100 is broken, the pump cell current Ip is kept around the oxygen concentration measuring range, thereby preventing an excess current from flowing through the pump cell 110. For example, on the lean side, the pump cell current Ip is limited at the point E, thereby undesirable heat from being produced by an excessive increase in the pump cell current Ip. This current limitation also serves to avoid an error in determining the impedance Rip of the pump cell 110. For example, if the senor 100 is broken in the absence of the current limitation, it will cause the current detected when the impedance Rip is determined to exceed greatly out of the oxygen concentration measuring range, thus resulting in failure in calculating the impedance Rip. The above current limitation avoids this problem.

The target applying voltage lines LX11 and LX12 may alternatively be primary lines extending in parallel to the abscissa axis of FIG. 10.

A gas concentration measuring apparatus according to the second embodiment will be described below.

When the gas concentration sensor 100 is actuated at the start of the engine, the first and second chambers 144 and 146 are filled with the air, so that a large quantity of oxygen exists (e.g., an oxygen concentration=20.9%). This means that an excessive quantity of oxygen ($O_2$) contributing to an error in determining the concentration of NOx is within the first and second chambers 144 and 146. In this case, when the voltage (e.g., when A/F=10 to the air, 0.1 to 0.7 V), as used in the first embodiment, is applied to the pump cell 110, 5 to 10 minutes are required to discharge the residual oxygen within the first and second chambers 144 and 146, thus resulting in a difficulty in determining the concentration of NOx quickly. In order to this problem, the gas concentration measuring apparatus of this embodiment is designed to apply a higher voltage (e.g., 0.8 to 1.2 V) to the pump cell 110 for one minute to enhance the ability of the pump cell 110 to discharge the oxygen within the first and second chambers 144 and 146 to the air passage 150.

Figure 11:
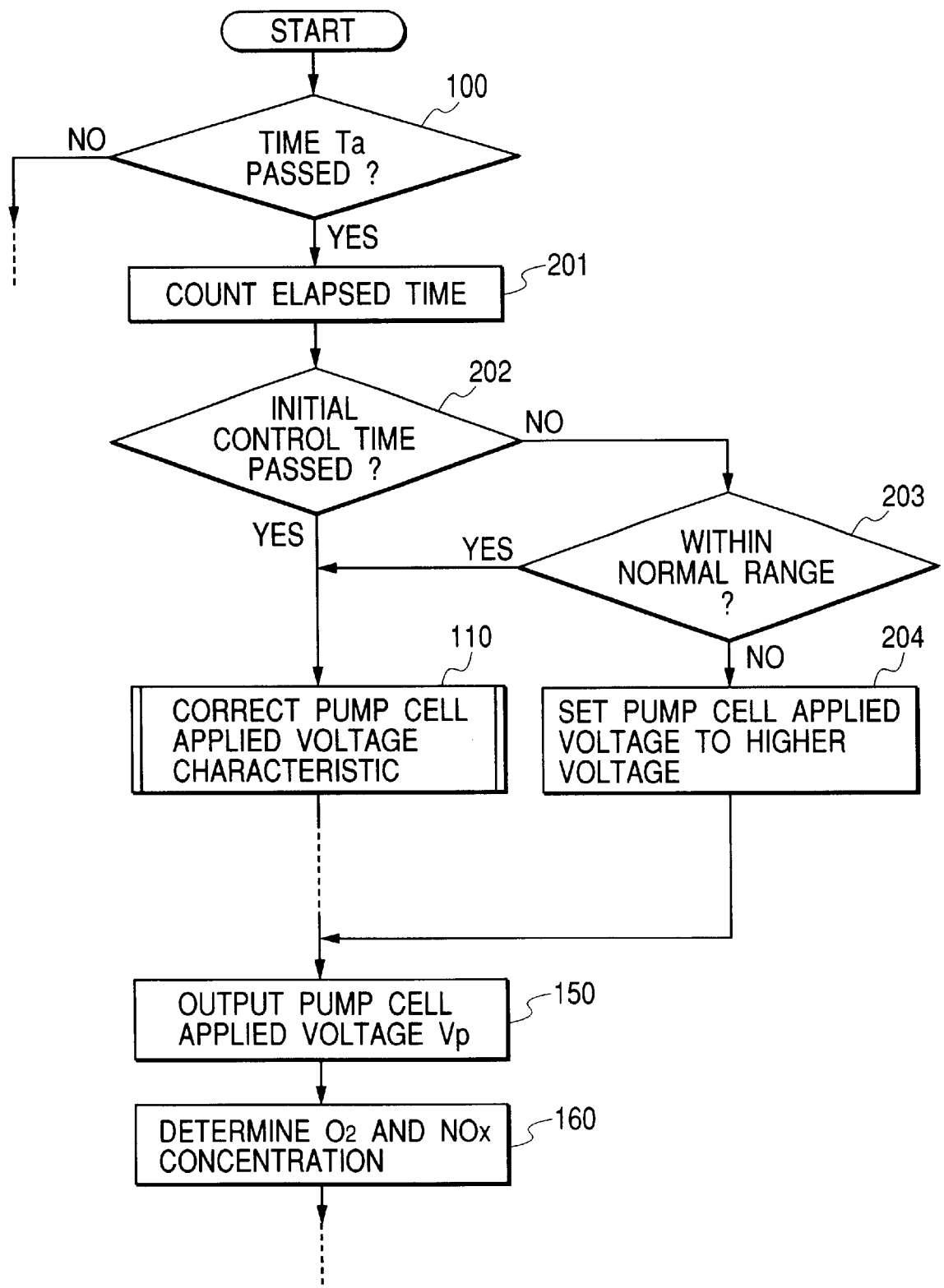
FIG. 11 is a flowchart of a program to control an operation of a gas concentration measuring apparatus according to the second embodiment of the invention.

The above operation will be described below in detail with reference to FIG. 11. The program of FIG. 11 is performed by the microcomputer 170 instead of the one shown in FIG. 6. The same step numbers as employed in FIG. 6 will refer to the same operations.

Upon turning on of the microcomputer 170, the routine enters the program and proceeds to step 100 wherein it is determined whether a preselected period of time Ta has elapsed after the concentrations of $O_2$ and NOx are measured in a previous cycle or not. If a YES answer is obtained, then the routine proceeds to step 201 wherein the elapsed time from start up of the engine is counted. The routine proceeds to step 202 wherein it is determined whether an initial control time, for example, one minute has passed or not. If a YES answer is obtained, then the routine proceeds to step 110 wherein the monitor cell current Im is monitored to correct the pump cell-applied voltage Vp to be applied to the pump cell 110 in the same manner as in the first embodiment.

Alternatively, if a NO answer is obtained in step 202, then the routine proceeds to step 203 wherein it is determined whether the monitor cell current Im indicates a normal value or not. This determination is made to determine whether the monitor cell current Im lies within a normal range or not. For example, if $Im \leq 4$ $\mu A$ meaning that the monitor cell current Im lies within the normal range, it is concluded that an excessive quantity of oxygen does not exist within the first and second chambers 144 and 146 even after the start up of the engine. For instance, such a condition is encountered when the engine is re-started immediately after the stop of the engine, and the routine proceeds to step 110.

Alternatively, if the monitor cell current Im lies out of the normal range (Im>4 $\mu A$), then the routine proceeds to step 204 wherein the pump cell-applied voltage Vp is set to a higher voltage (e.g., 0.8 to 1.2 V) required to enhance the ability of the pump cell 110 to discharge the oxygen within the first and second chambers 144 and 146 to the air passage 150.

After the pump cell-applied voltage Vp is determined in step 110 or 204, the routine proceeds to step 150 wherein the pump cell-applied voltage Vp is outputted to the pump cell 110. The routine proceeds to step 160 wherein after the pump cell current Ip is in a steady state following application of the pump cell-applied voltage Vp, the concentration of oxygen contained in the exhaust gasses is determined as a function of the pump cell current Ip. The concentration of NOx contained in the exhaust gasses is also determined as a function of the sensor cell current Is.

Other arrangements are identical with those in the first embodiment, and explanation thereof in detail will be omitted here.

A gas concentration measuring apparatus according to the third embodiment will be described below.

A change in impedance Rip of the pump cell 110 will cause the ability of the pump cell 110 to discharge the oxygen to the air passage 150 to be lowered even if the pump cell-applied voltage Vp is constant. In order to avoid this drawback, the gas concentration measuring apparatus of this embodiment is designed to correct the pump cell-applied voltage Vp to be applied to the pump cell 110 as a function of the impedance Rip of the pump cell 110.

Figure 12:
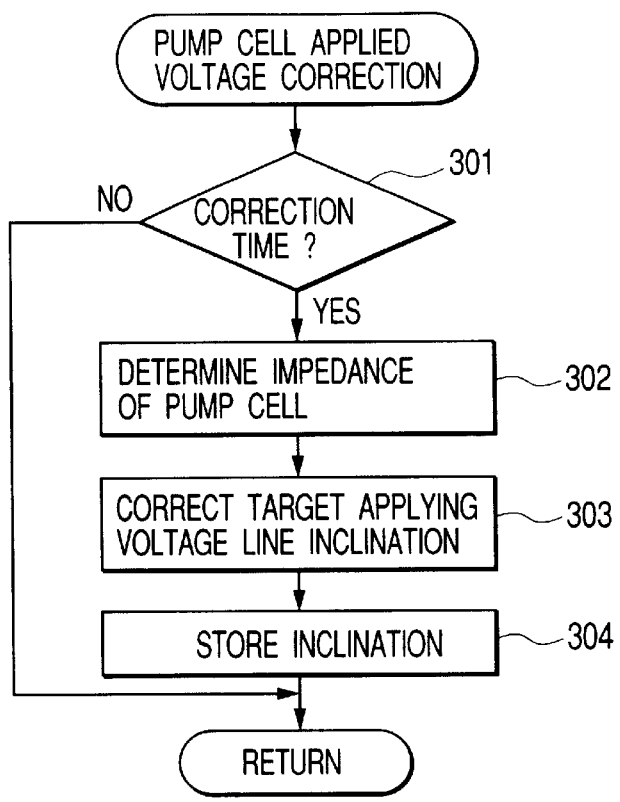
FIG. 12 is a flowchart of a program to correct the voltage to be applied to a pump cell according to the third embodiment of the invention.

Instead of the correction of the pump cell-applied voltage Vp performed in step 110 of FIG. 6 (i.e., the program of FIG. 7), a program, as shown in FIG. 12, is executed by the microcomputer 170.

First, in step 301, it is determined whether a correction time when the pump cell-applied voltage Vp should be corrected has been reached or not. For example, the correction time is set to an interval of ten to several hundreds msec.

If a YES answer is obtained in step 301, then the routine proceeds to step 302 wherein the impedance Rip of the pump cell 110 is determined in the same manner as described in the first embodiment. The routine proceeds to step 303 wherein the inclination of the target applying voltage line LX1 is corrected as a function of the impedance Rip of the pump cell 110. The routine proceeds to step 304 wherein the corrected inclination of the target applying voltage line LX1 of the V-I map for the pump cell 110 is stored in the memory of the microcomputer 170.

Figure 13:
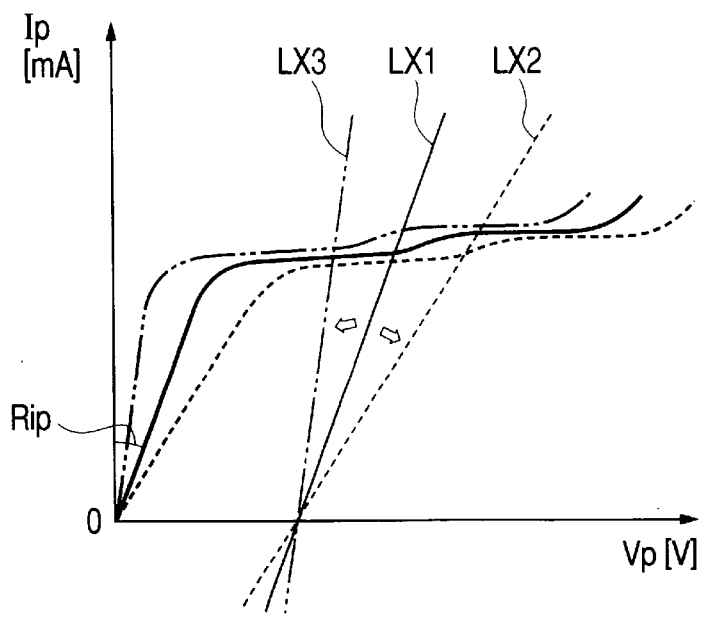
FIG. 13 shows a map for correcting the voltage to be applied to a pump cell as a function of the impedance of the pump cell.

The operation in step 303 will be described in detail with reference to FIG. 13.

If the impedance Rip is smaller than a given threshold value, the target applying voltage line LX1 of the V-I map is changed to LX2, thereby correcting the pump cell-applied voltage Vp in a direction in which the residual quantity of $O_2$ within the first chamber 144 is decreased. Alternatively, if the impedance Rip is greater than the given threshold value, the target applying voltage line LX1 is changed to LX3, thereby correcting the pump cell-applied voltage Vp in a direction in which the residual quantity of $O_2$ within the first chamber 144 is increased. This optimizes the residual quantity of $O_2$ within the first and second chambers 144 and 146, thereby resulting in improved accuracy of determining the concentration of NOx.

A gas concentration measuring apparatus according to the fourth embodiment will be described below which is different from the one in the first embodiment only in that an output of the sensor cell 130 is corrected as a function of the monitor cell current Im. Other arrangements are identical, and explanation thereof in detail will be omitted here.

Figure 14A:
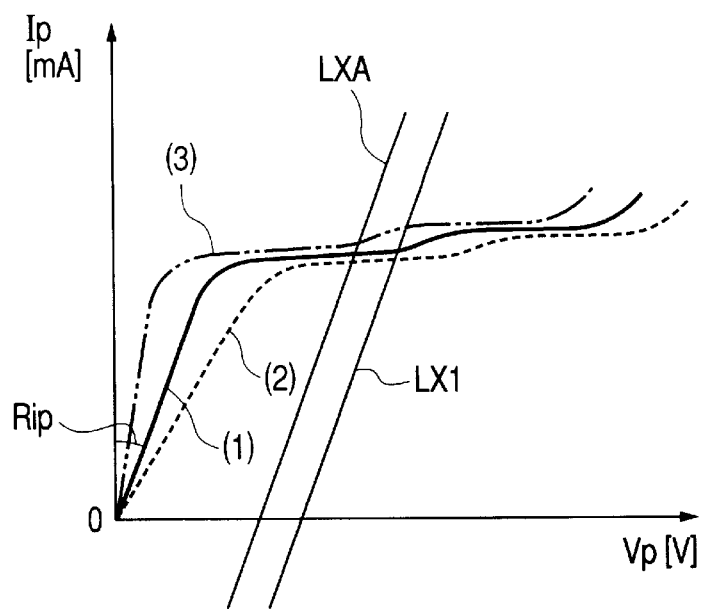
FIG. 14(a) is a map showing an applied voltage-to-output current relation of a pump cell which is used in correcting an output of a sensor cell as a function of an output current of a monitor cell according to the fourth embodiment of the invention.
Figure 14B:
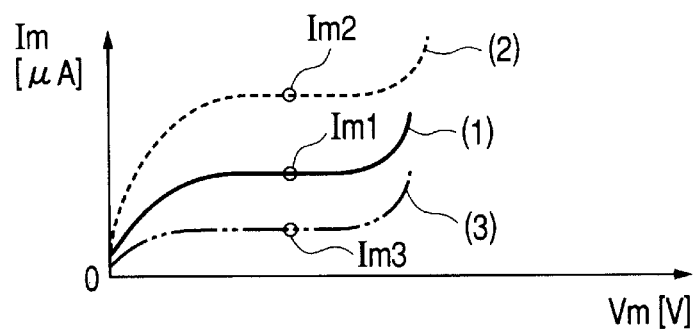
FIG. 14(b) shows a variation in output current of a monitor cell with a variation in impedance of a pump cell.
Figure 14C:
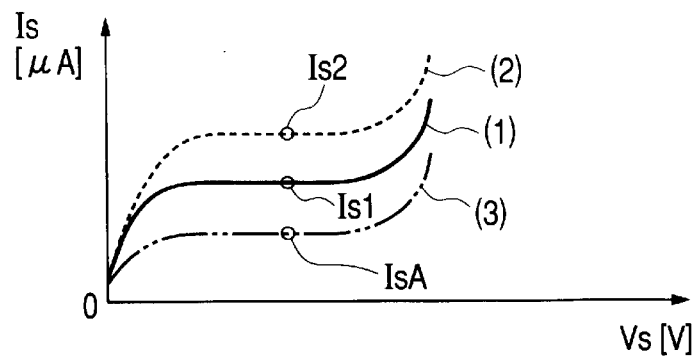
FIG. 14(c) shows a variation in output current of a sensor cell with a variation in impedance of a pump cell.

FIGS. 14(a), 14(b), and 14(c) show examples of the applied voltage characteristics or V-I relations between voltages applied to the pump cell 110, the monitor cell 120, and the sensor cell 130 and outputs thereof when the concentration of $O_2$ and NOx are, like the FIGS. 3(a) to 3(c), constant and that solid lines (1) denote the reference V-I curves in FIGS. 3(a), 3(b), and 3(c), respectively.

In FIG. 14(a), a target applying voltage line LXA is defined on a lower voltage side of the target applying voltage line LX1, as defined in FIG. 3(a). The pump cell-applied voltage Vp is determined on the target applying voltage line LXA. The shifting of the target applying voltage line LX1 to the lower voltage side means a slight increase in concentration of oxygen within the first and second chambers 144 and 146, thereby avoiding the decomposition of NOx in the pump cell 110 even if the impedance Rip of the pump cell 110 is increased undesirably due to, for example, a rise in temperature of exhaust gasses.

The first chamber 144 is, as described above, kept in concentration of oxygen at a constant level. The residual oxygen within the first chamber 144 flows into the second chamber 146. The sensor cell 130, thus, produces as the sensor cell current Im the sum of a current produced by decomposition of NOx and an offset current produced by the residual $O_2$ flowing into the second chamber 146. When the residual $O_2$ and the offset current are constant, it is possible to evaluate a relative concentration of NOx., but when the offset current changes with a change in residual quantity of $O_2$, it will result in an error in determining the concentration of NOx. For instance, when the impedance Rip is increased with a drop in temperature of exhaust gasses or greater than a reference value due to an inherent error of the gas concentration sensor 100, the V-I relation of the pump cell 110 changes from the solid line (1) to the broken line (2) in FIG. 14(a), which will cause the residual quantity of oxygen to increase within the first and second chambers 144 and 146. The increase in residual quantity of oxygen will cause the V-I relation of the monitor cell 120 to change, as shown in FIG. 14(b), from the solid line (1) to a broken line (2) (i.e., a change in monitor cell current from Im1 to Im2). Additionally, the quantity of $O_2$ to be dissociated by the sensor cell 130 together with NOx also increases, thereby causing the V-I relation of the sensor cell 130, as shown in FIG. 14(c), to be changed from the solid line (1) to a broken line (2), which leads to an error in determining the concentration of NOx. The sensor cell current Is2 contains an offset current equivalent to the monitor cell current Im2 which contributes to the error in determining the concentration of NOx. In order to avoid this drawback, the gas concentration measuring apparatus of this embodiment is designed to determine the residual quantity of oxygen using the monitor cell current Im and correct the sensor cell current Is.

Specifically, when the value of the monitor cell current Im indicates Im1 or Im2, it is subtracted from an actual value Is1 or Is2 of the sensor cell current Is. In either case, the sensor cell current Is is corrected to a value IsA which is produced only by decomposition of NOx without containing the offset current. Thus, when the concentration of NOx contained in exhaust gasses is constant, the sensor cell 130 continues to produce the sensor cell current Is at a constant level, thereby eliminating the error in determining the concentration of NOx.

Conversely, when the impedance Rip of the pump cell 110 is decreased with a rise in temperature of exhaust gasses or lower than the reference value due to an inherent error of the pump cell 110, it will cause the V-I relation, as expressed by the solid line (1) in FIG. 14(a), to be shifted to a two-dot chain line (3), thereby causing a small quantity of oxygen to remain in the first and second chambers 144 and 146. This causes the V-I relation of the monitor cell 120, as shown in FIG. 14(b), to be changed from the solid line (1) to a two-dot chain line (3) (i.e., a change in monitor cell current from Im1 to Im3), thereby resulting in a decreased effect of the offset current on the sensor cell current Is. The sensor cell current Is may not be corrected.

If the catalysis of the electrodes 121 and 122 of the monitor cell 120 is identical with that of the electrodes 131 and 132 of the sensor cell 130, that is, the electrodes 121 and 122 are identical in size and material with the electrodes 131 and 132, it is possible to eliminate the offset current only by subtracting the monitor cell current Im from the sensor cell current Is. However, if the catalysis of the electrodes 121 and 122 of the monitor cell 120 is different from that of the electrodes 131 and 132 of the sensor cell 130, it is advisable that either of the monitor cell current Im and the sensor cell current Is be multiplied by a given coefficient equivalent to a difference in catalysis between the monitor cell 120 and the sensor cell 130 to bring the monitor cell current Im and the sensor cell current Is produced by the same quantity of oxygen into agreement with each other.

Figure 15:
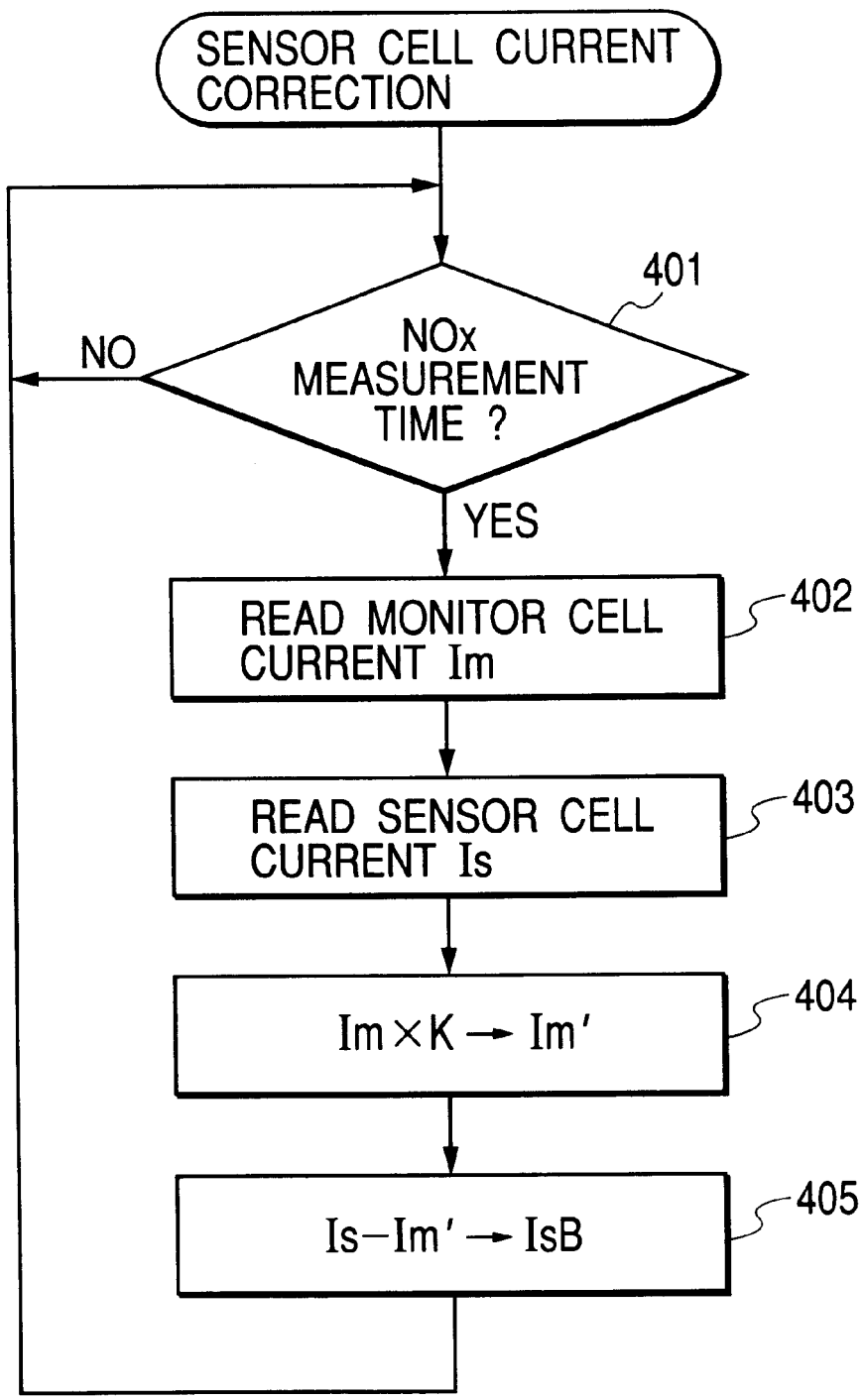
FIG. 15 is a flowchart of a program to correct an output current of a sensor cell as a function of an output current of a monitor cell according to the fourth embodiment of the invention.

The above correction of the sensor cell current Is is described in more detail with reference to a flowchart of FIG. 15.

First, in step 401, it is determined whether a measurement time when the concentration of NOx should be measured has been reached or not. For example, the measurement time is set to an interval of 8 msec.

If a YES answer is obtained in step 401, then the routine proceeds to step 402 wherein the monitor cell current Im is read out of the current detector 172. The routine proceeds to step 403 wherein the sensor cell current Is is read out of the current detector 173.

The routine proceeds to step 404 wherein the monitor cell current Im is multiplied by a coefficient K determined by differences in size and material of the electrodes 121 and 122 of the monitor cell 120 and the electrodes 131 and 132 of the sensor cell 130 to produce a corrected monitor cell current Im'. This eliminates the difference in catalysis between the monitor cell 120 ad the sensor cell 130. If the degree of catalysis of the electrodes 121 and 122 of the monitor cell 120 is identical with that of the electrodes 131 and 132 of the sensor cell 130, the coefficient K is set to one (1). The sensor cell current Is may alternatively be multiplied by the coefficient K.

The routine proceeds to step 405 wherein the corrected monitor cell current Im' is subtracted from the sensor cell current Is to determine a corrected sensor cell current IsB. This eliminates an error in determining the concentration of NOx arising from inclusion of the offset in the sensor cell current Is. In the example of FIG. 14(c), IsA is determined as the corrected sensor cell current IsB.

The above operations in steps 401 to 405 may be executed in step 160 of FIG. 6.

A gas concentration measuring apparatus according to the fifth embodiment of the invention will be described below which is designed to perform both the function of correcting the V-I relation defined in the map for the pump cell 110 based on the monitor cell current Im and the function of correcting an output of the sensor cell 130 based on the monitor cell current Im.

The gas concentration measuring apparatus works to monitor the monitor cell current Im to determine the residual quantity of oxygen within the second chamber 146 and correct the pump cell-applied voltage Vp as a function of the residual quantity of oxygen, thereby keeping the concentration of oxygen constant within the first and second chambers 144 and 146. The unit of current produced by the pump cell 110 as a function of the concentration of oxygen is mA (milli ampere), while the unit of current produced by the sensor cell 130 produced as a function of the concentration of NOx is μA (micro ampere). Specifically, the pump cell current Ip is greatly different in level from the sensor cell current Is. It is, thus, difficult for the pump cell 110 to discharge the oxygen to the air passage 150 completely without decomposing the NOx in terms of control resolution. Discharging the oxygen to the air passage 150 completely may result in decomposition of a small quantity of NOx, which will cause a great error to be added to the sensor cell current Is. The gas concentration measuring apparatus of this embodiment is, thus, designed to correct the pump cell-applied voltage Vp (i.e., the V-I map for the pump cell 110) to the extent that the pump cell 110 does not decompose NOx. This will cause a small quantity of oxygen to remain within the first and second chambers 144 and 146. The gas concentration measuring apparatus monitors the residual quantity of oxygen using the monitor cell current Im produced by the monitor cell 120 to correct the sensor cell current Is.

The above operations will be discussed in detail with reference to FIGS. 16(a), 16(b), and 16(c).

Figure 16A:
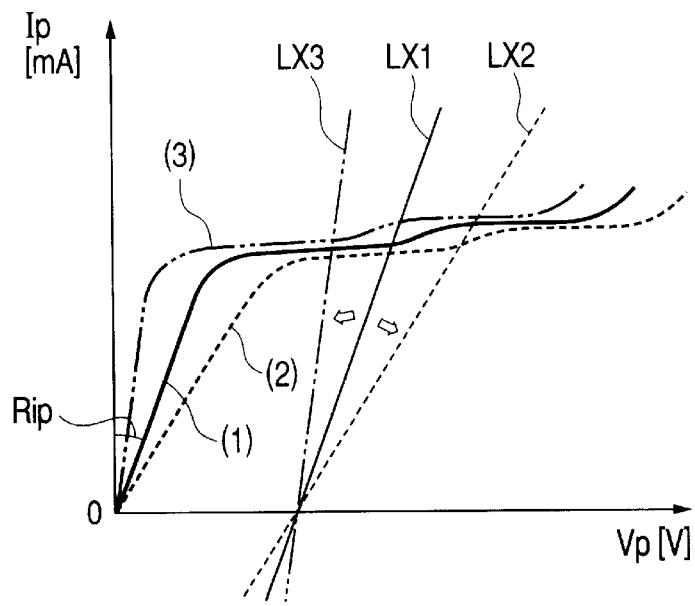
FIG. 16(a) is a map showing an applied voltage-to-output current relation of a pump cell which is used in correcting the voltage to be applied to a pump cell and an output of a sensor cell as a function of an output current of a monitor cell according to the fifth embodiment of the invention.
Figure 16B:
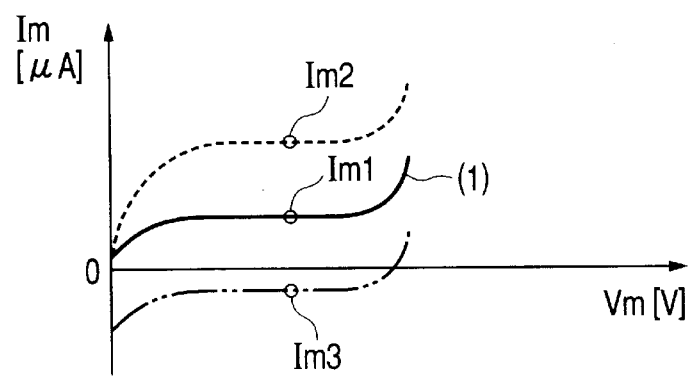
FIG. 16(b) shows a variation in output current of a monitor cell with a variation in impedance of a pump cell.
Figure 16C:
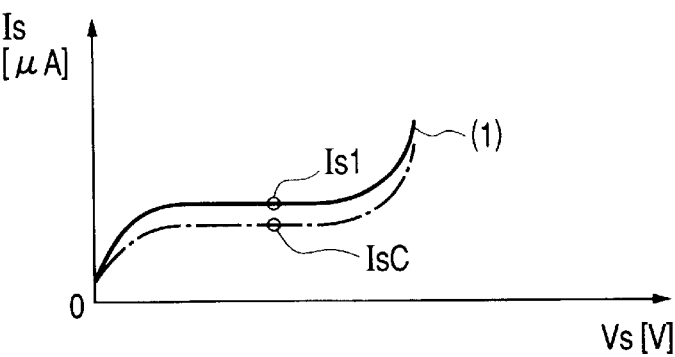
FIG. 16(c) shows a variation in output current of a sensor cell with a variation in impedance of a pump cell.

FIGS. 16(a), 16(b), and 16(c) show examples of the applied voltage characteristics or V-I relations between voltages applied to the pump cell 110, the monitor cell 120, and the sensor cell 130 and outputs thereof when the concentration of $O_2$ and NOx are, like the FIGS. 3(a) to 3(c), constant and that solid lines (1) denote the reference V-I curves in FIGS. 3(a), 3(b), and 3(c), respectively.

When the impedance Rip of the pump cell 110 is kept at a target value, so that it is unnecessary to correct the target applying voltage line LX1 in the V-I map for the pump cell 110, that is, when the pump cell 110 has the V-I relation, as indicated by (1) in FIG. 16(a), the pump cell-applied voltage Vp which does not induce the decomposition of NOx in the pump cell 110 is provided, thereby causing a small quantity of oxygen to flow into the second chamber 146. Thus, the monitor cell current Im produced by the monitor cell 120 has a value Im1, as indicated in FIG. 16(b), and the sensor cell current Is produced by the sensor cell 130 has a value Is1, as indicated in FIG. 16(c). The value Is1 contains an offset current component equivalent to the value Im1 of the monitor cell current Im. The microcomputer 170, thus, subtracts the offset current component from the value Is1 of the sensor cell current Is to derive a sensor current value IsC not including the offset current component.

When the impedance Rip is increased with a drop in temperature of exhaust gasses or greater than a reference value due to an inherent error of the gas concentration sensor 100, the V-I relation of the pump cell 110 changes from the solid line (1) to the broken line (2) in FIG. 16(a), the microcomputer 170 detects such a condition from the value Im2 of the monitor cell current Im and changes the target applying voltage line LX1 to LX2 in FIG. 16(a), thereby keeping the concentration of oxygen constant within the first and second chambers 144 and 146. The monitor cell 120 and the sensor cell 130 will, thus, have the V-I relations, as indicated by the solid lines (1) in FIGS. 16(b) and 16(c), respectively, thereby causing the sensor cell 130 to produce the current value Is1 in FIG. 16(c). The current value Is1, as described above, contains the offset current component. The microcomputer 170, thus, subtracts the offset current component from the current value Is1 to derive the current value IsC, thereby eliminating the error in determining the concentration of NOx.

Alternatively, when the impedance Rip of the pump cell 110 is decreased, the V-I relation of the pump cell 110 changes from the solid line (1) to the broken line (3) in FIG. 16(a). The microcomputer 170 detects such a condition from the monitor cell current Im3 and changes the target applying voltage line LX1 to LX3 in FIG. 16(a), thereby keeping the concentration of oxygen constant within the first and second chambers 144 and 146. The sensor cell 130 will, thus, have the V-I relation, as indicated by the solid line (1) in FIG. 16(c), thereby causing the sensor cell 130 to produce the current value Is1 in FIG. 16(c). The current value Is1, as described above, contains the offset current component. The microcomputer 170, thus, subtracts the offset current component from the current value Is1 to derive the current value IsC, thereby eliminating the error in determining the concentration of NOx.

Figure 17:
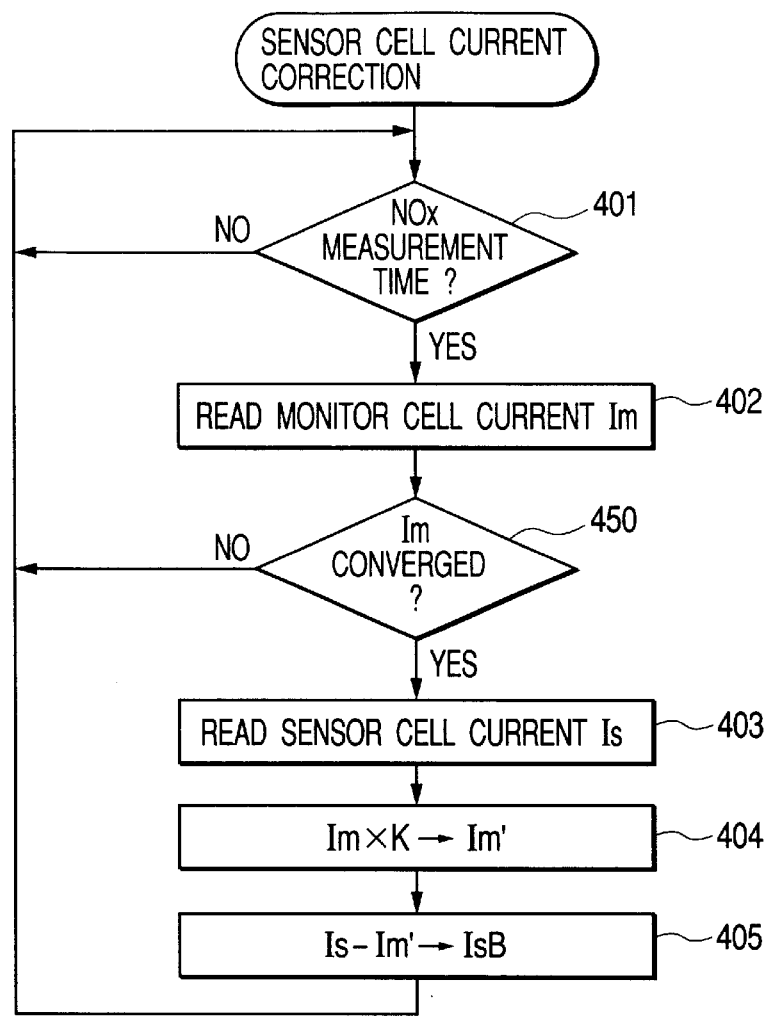
FIG. 17 is a flowchart of a program to correct the voltage to be applied to a pump cell and an output of a sensor cell as a function of an output current of a monitor cell according to the fifth embodiment of the invention.

The above operations are achieved in the microcomputer 170 by executing the program of FIG. 7, as described already, and a program, as shown in FIG. 17. Specifically, the microcomputer 170 executes the program of FIG. 7 to correct the target applying voltage line LX1 in the map for the pump cell 110 and update the pump cell-applied voltage Vp as a function of the pump cell current Ip at a cycle of 4 msec. The program of FIG. 17 is different from the one shown in FIG. 15 only in step 450. Specifically, after the monitor cell current Im is read out of the current detector 172 in step 402, the routine proceeds to step 450 wherein it is determined whether the monitor cell current Im has been converged on or fallen within a range around a target one or not. The pump cell-applied voltage Vp is corrected by the operation of FIG. 7 so as to bring the monitor cell current Im into agreement with the target monitor cell current Imtg which is set to, for example, 0.5 to 2 μA required for keeping the concentration of oxygen within the second chamber 146 at a given low oxygen level (e.g., near the stoichiometric). Therefore, if the monitor cell current Im has been bought into agreement the target monitor cell current Imtg, a YES answer is obtained in step 450, and the routine proceeds to step 403. Specifically, if the concentration of oxygen within the second chamber 146 is kept at a desired level, the routine proceeds to step 403 wherein the sensor cell current Is is read out of the current detector 173. Alternatively, if a NO answer is obtained in step 450, then the routine returns back to step 401. The following steps 404 and 405 are identical with those in FIG. 7, and explanation thereof in detail will be omitted here.

Instead of the program of FIG. 7, a program of FIG. 12 may be executed. Specifically, the microcomputer 170 corrects the V-I relation of the pump cell 110 as a function of the impedance Rip of the pump cell 110. This also enables the concentration of NOx to be determined accurately.

The gas concentration measuring apparatus of the fifth embodiment is also capable of avoiding undesirable oscillation of an applied voltage control circuit for the pump cell 110 which contributes to a great change in residual quantity of $O_2$ within the first and second chambers 144 and 146, thus eliminating the error in determining the concentration of NOx.

Further, the correction of the V-I map for the pump cell 110 is executed in a cycle of, for example, 10 to several hundreds msec., and the correction of the sensor cell current Is is carried out in a cycle of, for example, 8 msec. which are longer than that (e.g., 4 msec.) of control of the pump cell-applied voltage Vp. Specifically, such corrections are executed in a cycle determined by taking into consideration a change in response of the gas concentration sensor 100 due to deterioration or inherent error thereof, thereby minimizing undesirable oscillations of the control circuit during control of the applied voltage.

In the above embodiment, the correction of the pump cell-applied voltage Vp is, as described in FIGS. 5(a) to 5(c), achieved by changing the inclination of the target applying voltage line LX1, however, it may alternatively be accomplished by changing the offset b, as shown in FIG. 3(a). Specifically, when the impedance Rip is increased, for example, with a drop in temperature of exhaust gasses, the V-I relation of the pump cell 110 changes, as clearly shown in FIG. 18, from the solid line (1) to the broken line (2), the microcomputer 170 detects such an event from the monitor cell current Im and changes the target applying voltage line LX1 to LX10 in FIG. 18. Alternatively, when the impedance Rip of the pump cell 110 is decreased, it will cause the V-I relation of the pump cell 110 to change from the solid line (1) to the broken line (3) in FIG. 18. The microcomputer 170 detects such an event from the monitor cell current Im and changes the target applying voltage line LX1 to LX11. This keeps the concentration of oxygen constant within the second chambers 146, thus resulting in improved accuracy in determining the concentration of NOx.

Figure 19:
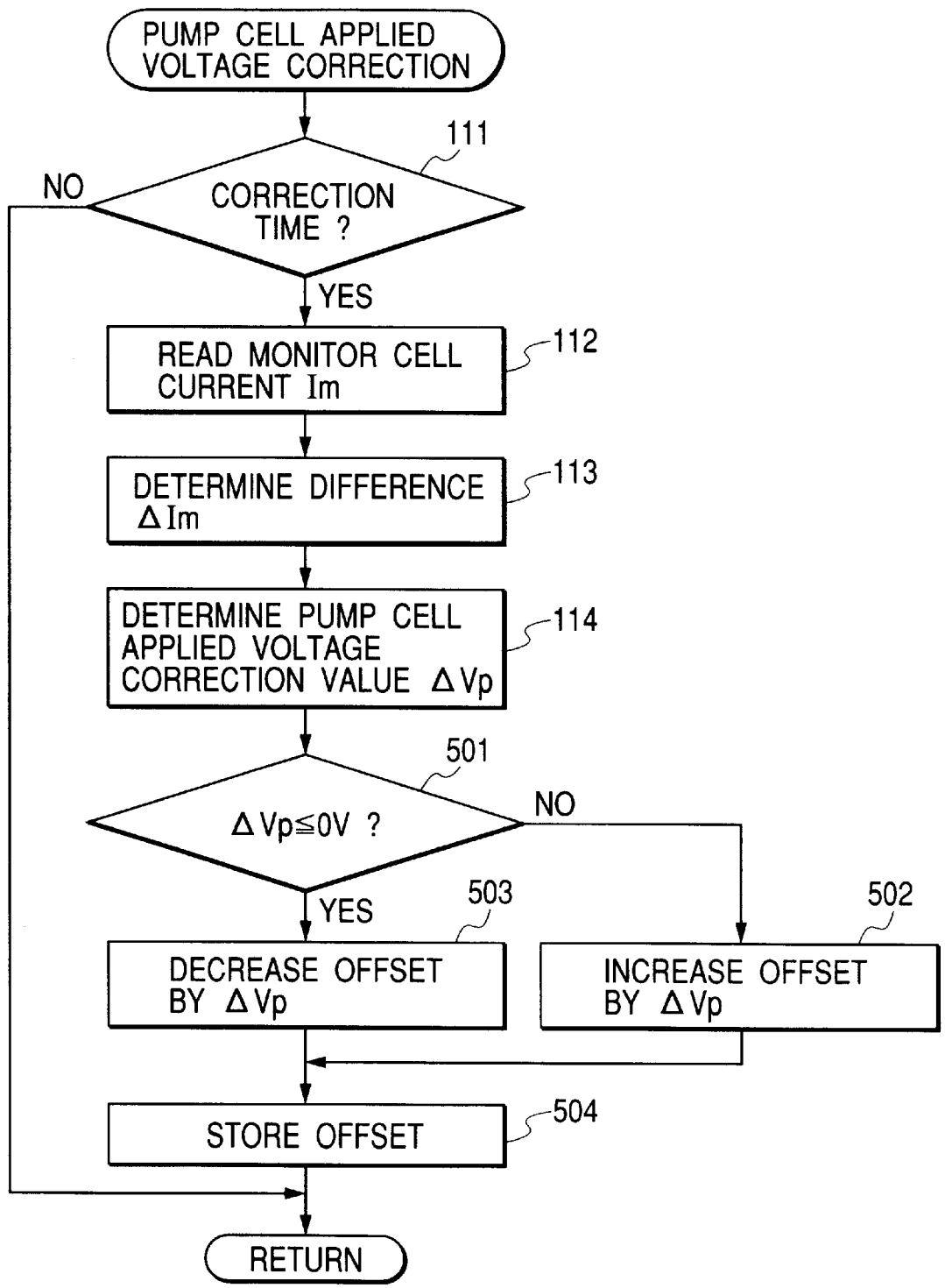
FIG. 19 is a flowchart of a program to correct the voltage to be applied to a pump cell using the map of FIG. 18.

The above operations will be described below in detail with reference to FIG. 19. Steps 111 to 114 are identical with those in FIG. 7.

After the correction value ΔVP of the pump cell-applied voltage Vp is determined as a function of the current difference Δ Im in step 144, the routine proceeds to step 501 wherein it is determined whether the correction value ΔVP is smaller than or equal to OV or not. If a NO answer is obtained (ΔVP>0), then the routine proceeds to step 502 wherein the offset b of the target applying voltage line LX1 is increased by the correction value ΔVP. Alternatively, if a YES answer is obtained in step 501 (ΔVP<0), then the routine proceeds to step 503 wherein the offset b of the target applying voltage line LX1 is decreased by the correction value ΔVP. After step 502 or 503, the routine proceeds to step 504 wherein the corrected offset b is stored in the memory of the microcomputer 170.

Figure 18:
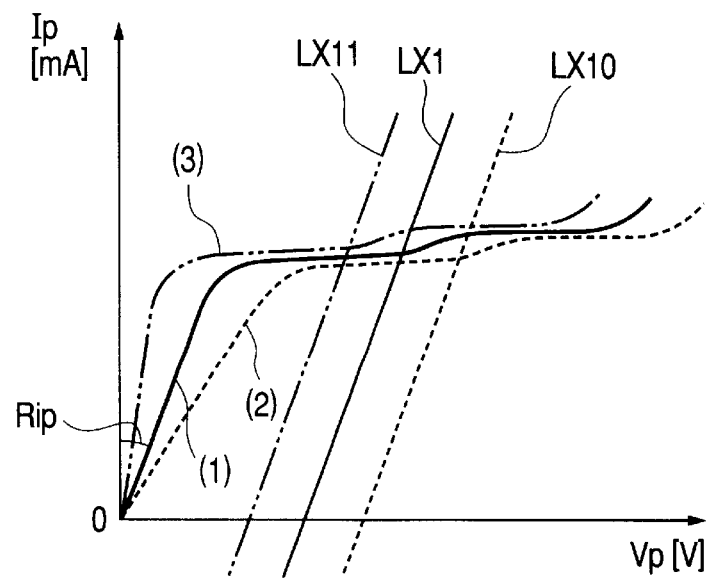
FIG. 18 is a modification of a map for correcting the voltage to be applied to a pump cell as a function of the impedance of the pump cell according to the fifth embodiment of the invention.

Specifically, step 502 changes the target applying voltage line LX1 to LX10 in FIG. 18, thereby correcting the pump cell-applied voltage Vp so as to decrease the residual quantity of oxygen in the first chamber 144. Step 503 changes the target applying voltage line LX1 to LX11 in FIG. 18, thereby correcting the pump cell-applied voltage Vp so as to increase the residual quantity of oxygen in the first chamber 144.

The above correction of the inclination of the target applying voltage line LX1 may alternatively be performed in the operation of FIG. 12 as a function of the impedance Rip of the pump cell 110. In this case, the offset b is increased with an increase in impedance Rip.

Instead of the correction of the target applying voltage line LX1, the pump cell-applied voltage Vp determined directly using the target applying voltage line LX1 may be corrected. For example, in place of steps 110 to 130 in FIG. 6, the pump cell-applied voltage Vp may be corrected as a function of the monitor cell current Im. Similar correction may be performed in the third embodiment in which the target applying voltage line LX1 is corrected as a function of the impedance Rip of the pump cell 110.

Figure 20:
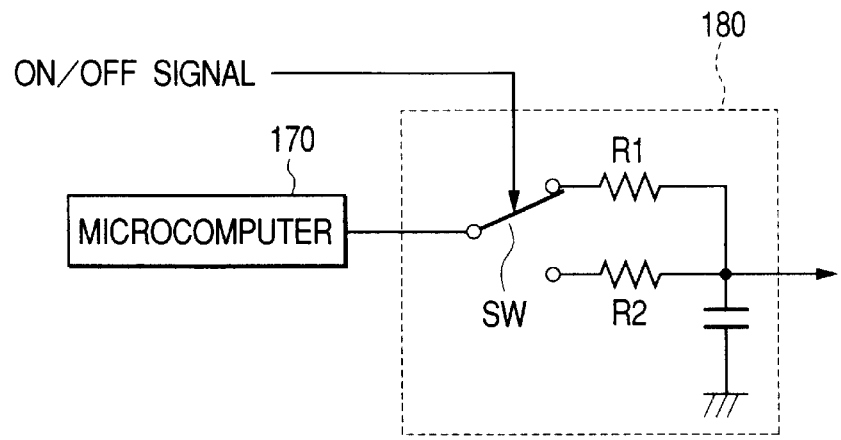
FIG. 20 is a circuit diagram which shows a modification of a low-pass filter of a gas concentration measuring apparatus.
Figure 23:
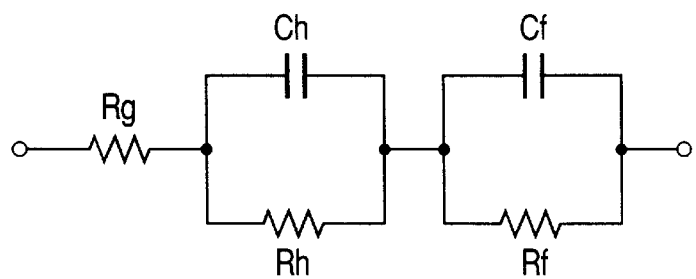
FIG. 23 shows an equivalent circuit of a gas concentration sensor of the invention.
Figure 24:
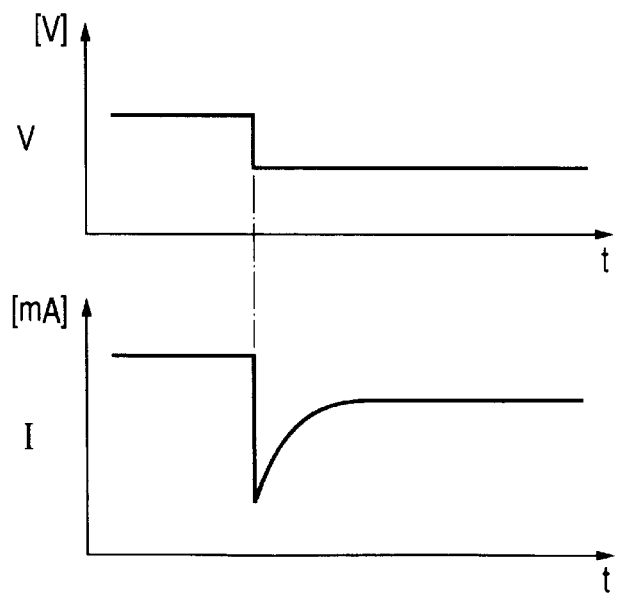
FIG. 24 shows a peak current output when the voltage applied to the sensor of FIG. 23 is changed.

FIG. 20 shows a modification of the low-pass filer 180 in which the time constant there of is changed between when the impedance Rip of the pump cell 110 is detected and when the concentration of a gas is measured.

The low-pass filter 180 consists of resistors R1 and R2 (R1 >R2) and a switch SW. When it is required to determine the concentration of oxygen, the microcomputer 170 outputs an off signal to the switch SW to establish connection between the resistor R1 and the microcomputer 170, thereby increasing the time constant. When it is required to determine the impedance Rip of the pump cell 110, the microcomputer 170 outputs an on signal to the switch SW to establish connection between the resistor R2 and the microcomputer 170, thereby decreasing the time constant. This enables the rate at which the pump cell-applied voltage Vp is applied to the pump cell 110 to be controlled variably.

The gas concentration measuring apparatus in each of the above described embodiments may be used with a gas concentration sensor 300 as shown in FIG. 21.

The gas concentration sensor 300 includes solid electrolyte bodies 301 and 302. The solid electrolyte body 301 has formed therein first and second pump cells 310 and 320. The solid electrolyte body 302 has formed therein a monitor cell 330 and a sensor cell 340. Between the solid electrolyte bodies 301 and 302, first and second chambers 303 and 304 which communicate with each other through an orifice 305 working as a diffusion path. The exhaust gasses are admitted into the first chamber 303 through a pinhole 306. Reference numbers 307 and 308 indicate air passages 307 and 308 are formed outside the solid electrolyte bodies 301 and 302. The reference number 309 denotes a heater.

The two pump cells 310 and 320 are provided for enhancing the pumping ability to pump the oxygen out of the first and second chambers 303 and 304 and the accuracy thereof.

The gas concentration measuring apparatus in each of the above described embodiments may also be used with a multi-cell gas concentration sensor having more than five cells.

A gas concentration sensor which is designed to decompose and discharge $O_2$ contained in gasses to be measured through a pump cell and decompose HC or CO contained in the gasses after the decomposition of $O_2$ through a sensor cell may be used in each of the above embodiments. Further, the gas concentration measuring apparatus in each of the above embodiments may also be used for measuring the concentration of gasses other than exhaust gasses of an automotive engine.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims. For example, the monitor cell 120 may alternatively be implemented by an oxygen concentration cell designed to produce an electromotive force as a function of oxygen ($O_2$).

What is claimed is:

1. A gas concentration measuring apparatus comprising:
   a gas concentration sensor including a gas chamber, a first cell responsive to application of a voltage to pump oxygen molecules selectively out of and into gasses admitted into the gas chamber to produce an electric current indicative of a concentration of the oxygen molecules, a second cell working to determine a concentration of a specified oxygen containing gas component contained in the gasses having passed through the first cell, and a monitor cell working to monitor a concentration of residual oxygen molecules within the gas chamber and provide an output indicative thereof;
   an applying voltage determining circuit looking up a predetermined voltage-to-current relation to determine a target voltage to be applied to said first cell as a function of the electric current produced by said first cell so as to preclude said first cell from decomposing the specified oxygen containing gas component; and an applying voltage controlling circuit working to apply the target voltage determined by said applying voltage determining circuit to said first cell.

2. A gas concentration measuring apparatus as set forth in claim 1, wherein the gas chamber includes a first chamber to which said first cell is exposed, a second chamber to which said monitor cell is exposed, and a diffusion path communicating between the first and second chambers.

3. A gas concentration measuring apparatus as set forth in claim 1, wherein the predetermined voltage-to-current relation is listed in a map, and wherein the applying voltage determining circuit determines the target voltage to be applied to said first cell by look-up using the map.

4. A gas concentration measuring apparatus as set forth in claim 1, further comprising an applying voltage correcting circuit working to correct the target voltage to be applied to said first cell as a function of a given residual oxygen variation factor of a variation in residual quantity of oxygen remaining within the gas chamber after said first cell pumps the oxygen molecules.

5. A gas concentration measuring apparatus as set forth in claim 4, wherein said applying voltage correcting circuit corrects the target voltage based on the output of said monitor cell.

6. A gas concentration measuring apparatus as set forth in claim 4, wherein said first cell is formed in a solid electrolyte element, further comprising a resistance measuring circuit working to measure a resistance of the solid electrolyte element, and wherein said applying voltage correcting circuit corrects the target voltage as a function of the resistance measured by said resistance measuring circuit.

7. A gas concentration measuring apparatus as set forth in claim 1, wherein said second cell outputs a current as a function of the concentration of the specified oxygen containing gas component, further comprising a second cell output correcting circuit working to correct the current outputted from said second cell based on the output of said monitor cell.

8. A gas concentration measuring apparatus as set forth in claim 1, further comprising a change rate determining circuit working to determine a variable rate at which the target voltage applied to said first cell is to be changed.

9. A gas concentration measuring apparatus as set forth in claim 8, wherein said change rate determining circuit increases the variable rate as a difference between an actual voltage applied to said first cell and the target voltage to be applied to said first cell increases.

10. A gas concentration measuring apparatus as set forth in claim 8, wherein said change rate determining circuit determines the variable rate by setting a cycle in which the target voltage is changed.

11. A gas concentration measuring apparatus as set forth in claim 10, said change rate determining circuit increases the cycle as a difference between an actual voltage applied to said first cell and the target voltage to be applied to said first cell is decreased.

12. A gas concentration measuring apparatus as set forth in claim 1, wherein a current measuring range is defined in which the electric current produced by said first cell is to be measured, and wherein the voltage-to-current relation is defined by a target applying voltage line representing the target applying voltage to be applied to said first cell in terms of the electric current produced by said first cell, the target applying voltage line including a segment which changes with a change in electric current produced by said first cell at a first inclination substantially depending upon a resistance of said first cell within the current measuring range, and wherein within an outside range defined outside the current measuring range, the target applying voltage line including a segment which changes at a second inclination reverse in sign to the first inclination.

13. A gas concentration measuring apparatus as set forth in claim 1, wherein a higher voltage is applied to said first cell for a period of time following energization of said gas concentration sensor.

14. A gas concentration measuring apparatus as set forth in claim 13, wherein when the output of said monitor cell falls out of a specified range immediately after said gas concentration is energized, said applying voltage controlling circuit applies the higher voltage to said first cell.

15. A gas concentration measuring apparatus as set forth in claim 1, wherein said monitor cell works to measure the concentration of residual oxygen molecules left in the gasses after the first cell has pumped the oxygen molecules out of or into the gasses.

16. A gas concentration measuring apparatus as set forth in claim 1, wherein the first cell is responsive to application of the voltage to pump the oxygen molecules out of the gasses within the gas chamber or into the gasses within the gas chamber from an ambient atmosphere to produce the electric current indicative of the concentration of the oxygen molecules.

17. A gas concentration measuring apparatus as set forth in claim 1, wherein the specified oxygen containing gas component is a NOx.

18. A gas concentration measuring apparatus comprising:
a gas concentration sensor including a gas chamber, a first cell responsive to application of a voltage to pump oxygen molecules selectively out of and into gasses admitted into the gas chamber to produce an electric current indicative of a concentration of the oxygen molecules, a second cell working to determine a concentration of a specified oxygen containing gas component contained in the gasses having passed through the first cell, and a monitor cell working to monitor a concentration of residual oxygen molecules within the gas chamber and provide an output indicative thereof;

an applying voltage correcting circuit working to determine a target voltage to be applied to said first cell by looking up a predetermined voltage-to-current relation as a function of the electric current produced by said first cell, said applying voltage correcting circuit correcting one of the target voltage and the predetermined voltage-to-current relation as a function of the output of said monitor cell; and an applying voltage controlling circuit working to control voltage applied to said first cell into agreement with the target voltage determined by said applying voltage correcting circuit.

19. A gas concentration measuring apparatus as set forth in claim 18, wherein the voltage-to-current relation is defined in a map by a target applying voltage line which represents the target applying voltage to be applied to said first cell in terms of the electric current produced by said first cell, and wherein said applying voltage correcting circuit corrects the voltage-to-current relation by changing an inclination of the target applying voltage line defined in the map as a function of the output of said monitor cell.

20. A gas concentration measuring apparatus as set forth in claim 18, wherein the voltage-to-current relation is defined in a map by a target applying voltage line which represents the target applying voltage to be applied to said first cell in terms of the electric current produced by said first cell, and wherein said applying voltage correcting circuit corrects the voltage-to-current relation by changing an offset of the target applying voltage line in terms of the electric current produced by said first cell as a function of the output of said monitor cell.

21. A gas concentration measuring apparatus as set forth in claim 18, wherein said applying voltage correcting circuit corrects the target voltage to be applied to the first cell so as to bring the output of said monitor cell into agreement with a target value required for keeping the concentration of oxygen molecules at a given level within the gas chamber.

22. A gas concentration measuring apparatus as set forth in claim 18, wherein correction of the target voltage to be applied to said first cell is performed in a cycle longer than that in which the voltage applied to said first cell is controlled by said applying voltage controlling circuit.

23. A gas concentration measuring apparatus comprising:
a gas concentration sensor including a gas chamber, a first cell responsive to an application of voltage to pump oxygen molecules selectively out of and into gasses admitted into the gas chamber to produce an electric current indicative of a concentration of the oxygen molecules, a second cell working to produce an electric current for determining a concentration of a specified oxygen containing gas component contained in the gasses having passed through the first cell, and a monitor cell working to monitor a concentration of residual oxygen molecules within the gas chamber and provide an output indicative thereof;
an applying voltage determining circuit looking up a predetermined voltage-to-current relation to determine a target voltage to be applied to said first cell as a function of the electric current produced by said first cell so as to preclude said first cell from decomposing the specified oxygen containing gas component; and
a second cell output correcting circuit working to correct the electric current outputted by said second cell as a function of the output of said monitor cell.

24. A gas concentration measuring apparatus as set forth in claim 23, wherein said second cell output correcting circuit subtracts a current value equivalent to the output of said monitor cell representing the concentration of residual oxygen molecules from the electric current produced by said second cell.

25. A gas concentration measuring apparatus as set forth in claim 24, wherein said second cell output correcting circuit corrects the electric current produced by said second cell and the output of said monitor cell as a function of a difference in catalysis between said second cell and said monitor cell, after which said second cell output correcting circuit subtracts the current value equivalent to the output of said monitor cell representing the concentration of residual oxygen molecules from the electric current produced by said second cell.

26. A gas concentration measuring apparatus as set forth in claim 20, wherein said second cell and said monitor cell are disposed adjacent to each other and exposed to a second chamber formed downstream of said first cell.

27. A gas concentration measuring apparatus comprising:
a gas concentration sensor including a gas chamber, a first cell responsive to application of a voltage to pump oxygen molecules selectively out of and into gasses admitted into the gas chamber to produce an electric current indicative of a concentration of the oxygen molecules, a second cell working to output an electric current for determining a concentration of a specified oxygen containing gas component contained in the gasses having passed through the first cell, and a monitor cell working to monitor a concentration of residual oxygen molecules within the gas chamber and provide an output indicative thereof;
an applying voltage determining circuit working to determine a target voltage to be applied to said first cell by looking up a predetermined voltage-to-current relation as a function of the electric current produced by said first cell;
a first correcting circuit working to correct on of the target voltage and the predetermined voltage-to-current relation as a function of the output of said monitor cell so as to preclude said first cell from decomposing the specified oxygen containing gas component;
an applying voltage controlling circuit working to control voltage applied to said first cell into agreement with the target voltage provided by said applying voltage correcting circuit; and
a second correcting circuit working to correct the electric current produced by said second cell as a function of the output of said monitor cell to determine the concentration of the specified oxygen containing gas component.

28. A gas concentration measuring apparatus as set forth in claim 27, wherein correction of the target voltage to be applied to said first cell is performed by said first correcting circuit in a cycle longer than that in which the voltage applied to said first cell is controlled by said applying voltage controlling circuit.

29. A gas concentration measuring apparatus as set forth in claim 27, wherein when the output of said monitor cell is brought into agreement with a target value or falls within a range around the target value under control of the target voltage applied to said first cell by said applying voltage controlling circuit, said second correcting circuit corrects the electric current produced by said second cell based on the output of said monitor cell.

30. A gas concentration measuring apparatus comprising:
a gas concentration sensor including a gas chamber, a first cell responsive to an application of a voltage to pump oxygen molecules selectively out of and into gasses admitted into the gas chamber to produce an electric current indicative of a concentration of the oxygen molecules, a second cell working to determine a concentration of a specified oxygen containing gas component contained in the gasses having passed through the first cell, and a monitor cell working to monitor a concentration of residual oxygen molecules within the gas chamber and provide an output indicative thereof, said first cell being formed in a solid electrolyte element;
a resistance determining circuit working to determine a resistance to the solid electrolyte element;
an applying voltage determining circuit working to determine a target voltage to be applied to said first cell by looking up a predetermined voltage-to-current relation as a function of the electric current produced by said first cell;
an applying voltage correcting circuit correcting one of the target voltage and the predetermined voltage-to-current relation as a function of the resistance determined by said resistance determining circuit; and
an applying voltage controlling circuit working to control voltage applied to said first cell into agreement with the target voltage provided by said applying voltage correcting circuit.

31. A gas concentration measuring apparatus as set forth in claim 30, wherein the voltage-to-current relation is defined in a map by a target applying voltage line which represents the target applying voltage to be applied to said first cell in terms of the electric current produced by said first cell, and wherein said applying voltage correcting circuit corrects the voltage-to-current relation by changing an inclination of the target applying voltage line defined in the map as a function of the resistance of said first cell.

32. A gas concentration measuring apparatus as set forth in claim 30, wherein the voltage-to-current relation is defined in a map by a target applying voltage line which represents the target applying voltage to be applied to said first cell in terms of the electric current produced by said first cell, and wherein said applying voltage correcting circuit corrects the voltage-to-current relation by changing an offset of the target applying voltage line in terms of the electric current produced by said first cell as a function of the resistance of said first cell.

* * * * *